United States Patent [19]

Vergara et al.

[11] Patent Number: 4,915,942
[45] Date of Patent: Apr. 10, 1990

[54] CROSS-REACTIVE AND PROTECTIVE EPITOPES OF CS

[75] Inventors: Ulises Vergara, Brooklyn; Andres Ruiz, Queens; Arturo Ferreira, New York; Ruth S. Nussenzweig, New York; Victor N. Nussenzweig, New York, all of N.Y.

[73] Assignee: New York University, New York, N.Y.

[21] Appl. No.: 115,634

[22] Filed: Oct. 26, 1987

Related U.S. Application Data

[63] Continuation of Ser. No. 649,903, Sep. 12, 1984.

[51] Int. Cl.$^4$ .................. C07K 7/00; A61K 35/74; A61K 37/02
[52] U.S. Cl. ..................... 424/88; 530/300; 530/350; 530/820; 530/806; 530/325; 530/326; 530/327; 530/825; 514/2; 514/12; 514/13; 514/14; 435/69.3; 424/85.8
[58] Field of Search .............. 424/88; 514/2, 12, 13, 514/14; 530/300, 350, 820, 806, 807, 325, 326, 327, 333, 825; 435/68, 70

[56] References Cited

U.S. PATENT DOCUMENTS 4,466,917 8/1984 Nussenzweig .................. 260/112 R

OTHER PUBLICATIONS

Hopp, T. P. et al, Proc. Natl. Acad. Sci, USA, 78:3824–3828 (6-1981).
Nardin, E. H. et al, J. Experimental Medicine 156:20–30 (Jul. 1982).
Cochrane, A. H. et al, Proc. Natl. Acad. Sci, USA, 79:5651–5655 (9-1982).
Goman, M. et al, Molecular and Biochemical Parasitology, 5:391–400 (1982).
Scaife, J. et al, J. Cellular Biochemistry, Supp. No. 7, Part A, p. 3, Abstract 0004 (1983).
Bone, N. et al, Serono Symp. Publ., Raven Press (1983), 2:125–134 cited in Chemical Abstract 98:192681r (1983).
Ellis, J. et al, Nature 302:536–538 (Apr. 1983).
Godson, G. N. et al, Nature 305:29–33 (Sep. 1983).
Enea, V. et al, Science 225:628–630 (Aug. 1984).
Dame, J. B. et al, Science 225:593–599 (Aug. 1984).
Hyde, J. E. et al, Molecular and Biochemical Parasitology 10:269–285 (1984).
Gysin, J. et al, J. Experimental Medicine 160:935–940 (Sep. 1984).
Zavala, F. et al, Federation Proceedings, Amer. Soc. Exp. Biol. 43:1808, Abstract 2288 (May 1984).
Zavala, F. et al, Science 228:1436–1440 (Jun. 1985).
Coppel, R. L. et al, Nature 306:751–756, (Dec. 1983).
Santoro, F. et al, J. of Biological Chemistry 258:3341–3345 (Mar. 1983).
Cochrane, A. H. et al, J. of Immunological Methods 71:241–245 (1984).
Ravetch, J. V. et al, Biotechnology 3:729–740 (1985). A review.
Ballou, W. R. et al, Science 228:996–999 (1985).
Vergara, U. et al, Molecular and Biochemical Parasitology 14:283–292 (1985).
Smith, G. L. et al, Science, 224:397–399 (4-1984).
Godson, G. N. et al, *Molecular Parasitology*, 3rd, J. T. August, ed. Academic Press, Orlando (1984), pp. 127–142.
Godson, G. N. et al, Philosoph. Trans. R. Soc. London, B, 307 (1131):129–139 (1984).
Meuwissen, J. H., Acta Leidensia, 52:19–29 (1984), A review.
Ozaki, L. S. et al, Cell 34(3):815–822 (1983).
Lupski, J. R. et al, Science 220:1285–1288 (6-1983).
Lerner, R. A., Scientific American (1983).

Primary Examiner—Margaret Moskowitz
Assistant Examiner—Jeff Kushan
Attorney, Agent, or Firm—Darby & Darby

[57] ABSTRACT

Synthetic peptides containing non-repeating epitopes of circumsporozoite derived protein antigen and which are substantially shorter in length than the intact antigen are disclosed. The peptides when administered to a host raise antibodies in that host that will bind to the circumsporozoite antigen on the parasite. Vaccines based upon these peptides, as well as means of raising antibodies to circumsporozoite antigens using the synthetic peptides are also disclosed.

24 Claims, 3 Drawing Sheets

FIG.1

P.knowlesi CIRCUMSPOROZOITE PROTEIN

...PKKPNENKLK QPNE.... 86    99    N2

...GQPQAQGDGANA...

C-C......RRKAHAGNKKAEDLTMDDLE...C-C
301 305         312                              331 335 340

C2

Signal Sequence: 1–18
Charged Area: 64–100
Repeats: 100–243
Charged Area: 305–335
Anchor Sequence: 343–353

N-Terminal
C-Terminal

ALIGNMENT OF THE N2 and C2 SEQUENCES OF P.knowlesi AND P.falciparum

CROSS-REACTIVE AND PROTECTIVE EPITOPES OF CS

The government has rights to this invention based on research support in the form of Grant N. AID-DPE-0453-C-00-2002-00 from the Department of State, Agency for International Development.

This is a continuation of application Ser. No. 649,903, filed Sept. 12, 1984.

BACKGROUND OF THE INVENTION

The present invention relates to polypeptide antigens suitable for providing protective immunity against malaria by incorporation into a vaccine. These antigens have amino acid sequences corresponding to segments of the amino acid sequence of the circumsporozoite protein that lie outside the bounds of the tandemly repeated domain of such protein. The antigens of the present invention can be used to elicit formation of antibodies, which recognize sporozoites not only of the same species of plasmodium from which these antigens were derived, but of other species as well.

The present application incorporates by reference the entire disclosures of:

(a) U.S. Pat. No. 4,466,917 of Nussenzweig, R., et al., issued on Aug. 21, 1984;

(b) assignee's copending U.S. patent application No. 99,652 filed Sept. 21, 1987 as a 37 CFR §1.62 continuation of application Ser. No. 574,553 of Ellis, J. et al., filed on Jan. 27, 1984 and entitled Protective Peptide Antigen; and (c) assignee's copending U.S. patent application No. 77,006 filed July 21, 1987 as a 37 CFR §1.62 continuation of application Ser. No. 633,147 of Ellis, J. et al., filed on July 23, 1984 and entitled Protective Peptide Antigen Corresponding to Plasmodium Falciparum Circumsporozoite Protein.

In most instances, malaria infections are initiated by the introduction of sporozoites (highly immunogenic forms of the malaria parasite) into the bloodstream of a host through the bite of an infected mosquito. The immunogenicity of sporozoites resides largely, if not exclusively, in a single antigen, the circumsporozoite (CS) protein (described in detail by F. Zavala, A. H. Cochrane, E. H. Nardin, R. S. Nussenzweig and V. Nussenzweig in an article in J. Exp. Med. 157: 1947 (1983). G. N. Godson, et al., Nature 305: 29 (1983) reported that the immunogenicity of the CS protein is restricted almost entirely to a single epitope which is identically or quasi-identically repeated several times in tandem. See also V. Enea, et al. Proc. Nat'l Acad. Sci. (accepted for publication, 1984).

Circumsporozoite proteins (CS proteins) are members of a family of polypeptides comprising the surface membranes of mosquito salivary gland sporozoites of mammalian malaria parasites of the genus plasmodium. The strong immunogenic properties of sporozoites are associated mainly with the CS protein. This protein, specific for the sporozoite stage, has an immunodominant region of repetitive epitopes. The repeated sequence from N to C terminus of the CS protein for *P. knowlesi* is Gln-Ala-Gln-Gly-Asp-Gly-Ala-Asn-Gly-Gln-Pro (also designated as QAQGDGANGQP) and the repeated tetrapeptide sequence of the CS protein for *P. falciparum* is Asn-Ala-Asn-Pro (also designated as NANP). Synthetic peptides consisting of multiples or analogs of the repeated amino acid sequences have been shown to be antigenic and are useful in the development of a malaria vaccine. Unfortunately, however, peptides derived from the immunodominant region of the CS protein display very little homology among themselves and only species-specific antigenicity.

Due to the immunodominance of the repetitive epitopes of the CS protein, it had not heretofore been possible to determine if other segments of the CS protein, which are not within the repetitive domain sequence, can induce antibodies affecting the viability of the parasite. Clearly, immunogenicity itself does not establish the utility of peptides having the sequence of such non-repeating segments as protective antigens against sporozoites, since such segments would need to be on an exposed surface of the CS molecule to allow recognition by antibodies.

OBJECTS OF THE INVENTION

It is an object of this invention to identify regions of the circumsporozoite surface proteins of a member of the genus plasmodium, other than the region containing the repetitive epitope, that contain other, non-repetitive epitopes for such protein.

Another object of this invention is to identify the non-repetitive epitopes of the CS protein, as a prerequisite for the development of an anti-malaria vaccine.

Yet another object of this invention is to identify and synthesize peptides (corresponding to the non-repetitive epitopes of the CS protein) that can elicit formation of antibodies in mammals which can in turn recognize the CS protein, in particular, the CS protein on the surface of sporozoites.

A further object of this invention is to identify and synthesize peptides capable of eliciting formation of antibodies that recognize the CS protein of more than one species of the genus plasmodium.

A further object of this invention is to identify such peptides as a prerequisite for the development of a synthetic malaria vaccine.

A still further object of this invention is to develop an immunogenic element for use in a malaria vaccine for administration to mammals.

SUMMARY OF THE INVENTION

This invention is directed to a peptide comprising an amino acid sequence corresponding to an epitope of a circumsporozoite surface protein of a member of the genus plasmodium, other than the repetitive immunodominant epitope of such protein. The peptide is capable of eliciting formation of antibodies in a host that recognize the circumsporozoite surface protein.

The peptides of the present invention are recognized by, and elicit formation of, antibodies that bind to the CS proteins of the malarial species from which they were derived and also to the CS proteins of other malarial species. This is so because segments of the sequence of CS proteins outside the immunodominant regiion are extensively homologous. Once one such peptide has been identified, the amino acid (and nucleotide) sequence of other peptides having the same properties can be readily identified by comparing the sequences of CS proteins of different species. These peptides are useful elements in the development of a synthetic malaria vaccine. They can be made by synthetic method, of they can form part of genetically engineered constructs.

BRIEF DESCRIPTION OF THE DRAWING

FIG. 1 is a schematic representation of the sequence of the intracellular precursor of *P. knowlesi* CS protein.

DETAILED DESCRIPTION OF THE INVENTION

Figure 2:
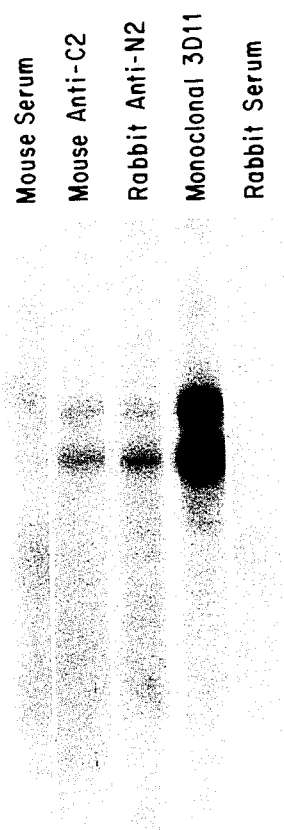
FIG. 2 is an autoradiograph of Western blotting (immunoblotting) of antibodies to synthetic peptides N2 and C2 of the present invention with *P. berghei* sporozoite extracts.

The primary structure of the CS protein for *P. knowlesi* and *P. falciparum* was first deduced from the nucleotide sequences of these proteins (Godson, G. N., et al., Nature, 305: 29 (September 1983) and Dame, J. B., et al., *Science*, 225: 593 (1984)). A schematic representation of the intracellular precursor of *P. knowlesi* CS protein is shown in FIG. 1. Two regions of this protein contain a large number of charged residues (these regions ae labeled "charged" in FIG. 1) and may contain an alpha-helical structure. One charged region at the amino terminal (N-terminus) end of the protein flanks the domain (segment) containing the tandem amino acid repeats. The other charged region, close to the C-terminus, is flanked on each side by a pair of cysteine residues.

Peptides having an amino acid sequence corresponding to these charged regions have been synthesized. The polar character of the charged regions indictes that they should be exposed on the surface of the CS molecule. Certain of these peptides are recognized by polyclonal antibodies raised against sporozoites (Vergara, et al., Mol. & Bioch. Parasitol., 1984, in press). Polyclonal antibodies raised against these peptides also recognize and bind authentic *P. knowlesi* CS protein on the surface of sporozoites, demonstrating the immunogenic properties of such peptides. Antibodies to N2 and C2 peptides (FIG. 1), react on the surface of sporozoites of *P. falciparum, P. vivax, P. malariae, P. brasilianum, P. bergei,* and *P. cynomolgi.*

The data demonstrate that the immogenic peptides correspond (or are closely related) to the corresponding exposed exterior segments of the CS molecule of most or all species of sporozoits from malaria parasites, and are not excised during intracellular processing of the CS molecule.

Comparison of the N2 and C2 peptides with the corresponding region of *P. falciparum* CS protein, as published in Dame et al, supra, shows a high degree of homology. Significantly, anti-sera raised against these peptides recognize the sporozoites of other species of the plasmodium genus as well.

The partial neutralization by a rabbit antiserum to one of these peptides (N2 in FIG. 1) of the infectivity of sporozoites from an heterologous species, *P. berghei,* demonstrates the presence of a related structure in corresponding regions of CS proteins of this species and that the N2 region is highly conserved in evolution.

Previous evidence shows that antibodies to the repetitive domain of CS protein neutralize infectivity of sporozoites of the species containing that CS protein and suggests that synthetic peptides incorporating the epitope of this repetitive domain could be used in species-specific vaccine preparations. The present invention leads to the conclusion that synthetic polypeptides, or conjugates and/or genetic engineering constructs incorporating the sequence of other peptides, which represent conserved (not species-specific) and exposed regions of the CS molecule, will protect a host against infection by any of several different species of malaria parasites.

EXAMPLE 1: ANTI-SPOROZOITE POLYCLONAL ANTIBODIES

Sporozoites of *P. knowlesi* were obtained from mosquito salivary glands from 10 to 18 days after an infective blood meal, according to the method of Vandenberg, J. P. et al., *Further Studies on the Plasmodium Berghei—Anopheles Stephensi—Rodent System of Mammalian Parasite,* J. Parasitol. 54: 1009–1016 (1968). These sporozoites were used to elicit polyclonal antibodies in a rabbit by ten intravenous injections of $10^6$–$10^7$ live sporozoites over a period of three months.

EXAMPLE 2: PEPTIDE SYNTHESIS

Several peptides were chosen for synthesis and immunization. The first was a tetraicosapeptide consisting of a dimer of the repetitive dodecapeptide of the *P. knowlesi* CS protein. This dodecapeptide is designated by the dotted boxes in FIG. 1. The synthesized tetraicosapeptide will be termed "2x repeat". The 2x repeat is a dimer of the amino acid sequence (from N to C terminal) Gln-Ala-Gln-Gly-Asp-Gly-Ala-Asn-Ala-Gly-Gln-Pro.

Two other peptides correspond to segments of the CS protein found in the domains labelled "charged" in FIG. 1. The first one, designated $N_2$, corresponds to amino acids 86–99 in FIG. 1 and has the amino acid sequence Pro-Lys-Lys-Pro Asn-Glu-Asn-Lys-Leu-Lys-Gln-Pro-Asn-Glu also designated as PKKPNENKLKQPNE). The second one, designated $C_2$, corresponds to amino acids 312–331 of the CS protein and has the amino acid sequence Arg-Arg-Lys-Ala-His-Ala-Gly-Asn-Lys-Lys-Ala-Glu-Asp-Leu-Thr-Met-Asp-Asp-Leu-Glu (also designated as RRKAHAGNKKAEDLTMDDLE).

Finally, two additional peptides were synthesized, termed $C_1$ and "charged". The sequence of $C_1$ was taken from the region immediately adjacent to the repeats towards the C terminal. Its overall amino acid composition resembles that of the repeats. The "charged" peptide corresponds to the sequence immediately following $N_2$ towards the N terminal within the charged region. The sequence of $C_1$ is Gly-Lys-Gly-Ala-Gln-Lys-Asn-Gly-Glu-Asn-Gly-Gly-Ala-Pro-Ala-Gly-Gly-Gly-Asn-Arg-Gly-Gln-Arg (also designated as GKGAQKNGENGGAPAGGNRGQR). The sequence of "charged" is Lys-Pro-Glu-Glu-Glu-Lys-Glu-Lys-Gly-Lys-Glu-Lys-Lys-Lys-Glu-Lys-Asp-Ala-Gly-Glu-Lys-Pro-Lys-Glu-Gly (also designated as KPEEEKEKGKEKKKEKDAGEKPKEG).

All peptides were synthesized on a Vega Model 250C automated synthesizer (Vega Bio-Chemicals, Inc., Tuscon, Ariz.) controlled by a Motorola computer with a program based on that of Merrified, R. B., Fed. Proc. 21: 412 (1962); J. Am. Chem. Soc. 85: 2149 (1963).

The synthesis of the dodecapeptide (1× repeat), set forth below, is typical of all peptide synthesis. Three grams of benzhydrylamine resin were suspended and washed three times with methylene chloride ($CH_2Cl_2$), three times with ethanol, and three more times with methylene chloride after placement in the synthesizer.

After a total wash of 2 minutes, the resin was treated with 50% trifluoroacetic acid containing 10% anisole in $CH_2Cl_2$ for 30 min., washed ten times with $CH_2Cl_2$, and neutralized by washing twice with 10% diisopropylethylamine in methylene chloride. The first BOC amino acid was coupled for one hour to the resin using 3-fold molar excess of dicyclohexyl carbodiimide, in the presence of a 3 molar excess of hydroxybenzotriazole in methylene chloride. Additional aliquots, one of hydroxybenzotriazole and one of diisopropylethylamine, were added at a 3-fold molar excess to BOC-amino acid for an additional hour. The resin was then washed in methylene chloride (3×), absolute ethanol (3×) and methylene chloride (3×), and an aliquot of the mixture was tested using the Kaiser ninhydrin procedure (Kaiser, E. et al., Analyt. Biochem. 34: 595 (1970). The resulting peptide was BOC-Gln(NPE)-Ala-Gln(NPE)-Gly-Asp(OBZ)-Gly-Ala-Asn(NPE)-Ala-Gly-Gln(NPE)-Pro-Co-BHA. The protected peptide resin was removed and saved for HF cleavage.

Cleavage was performed in a Penninsula HF apparatus (Penninsula, Laboratory, San Carlos, Calif.) in the presence of anisole (1.2 ml/mg resin) and methylethyl sulfide (1 ml/mg) at 0° C. for one hour, after which the mixture was thoroughly dried under high vacuum. The mixture was then washed with cold anhydrous ether, extracted with alternate washes of water and glacial acetic acid and lyophilized.

The crude peptides (200 mg aliquots) were desalted by gel filtration on a Sephadex G-25 column (120×2.0 cm) that had been equilibrated with $0.1NH_4HCO_3$, pH 8.0. The column effluent was monitored by UV absorbance at 254 and 206 nm with an LKB UV-Cord III monitor. The collected peptides were then characterized.

EXAMPLE 3: PURIFICATION OF ANTIBODIES CAPABLE OF REACTING WITH SPECIFIC SYNTHETIC PEPTIDES

Polyclonal antibodies recognizing the peptides were isolated from the anti-sporozoite rabbit antisera prepared in Example 1. The peptides were coupled to activated Sepharose-4B beads (Pharmacia Fine Chemical Company, Piscataway, N.J.) according to the manufacturer's instructions. The beads were subsequently treated for one hour with 0.005M glutaraldehyde in 0.25M $NaHCO_3$, pH 8.8. The washed beads were incubated with 1M ethanolamine, pH 9.0, for one hour, washed again in and resuspended in phosphate-buffered saline (PBS), pH 7.4.

To remove any non-specific binding substances, the anti-knowlesi antiserum was first adsorbed with beads conjugated to a non-relevant peptide. For example, to purify anti-$C_2$ antibodies, a sample of antiserum was sequentially adsorbed with N2-bearing beads, then with beads bearing peptides corresponding to other segments of the charged regions, and, finally with repeat-bearing beads. The supernatant resulting from the last adsorption was then incubated for several hours at room temperature with beads containing the peptide of interest. After washing repeatedly with PBS, the bound antibodies were eluted from the beads by treatment with 3M potassium thiocyanate. The eluate was immediately filtered through a small Sephadex G-25 column to remove small molecules. These purified antibodies were used to assay the synthetic peptides.

EXAMPLE 4: IMMUNORADIOMETRIC ASSAY

Synthetic peptides $N_2$, $C_2$ "charged" (corresponding to amino acids 99-86 of the *P. knowlesi* CS protein), C1 (corresponding to amino acids 267-245) and "2× repeat" were prepared in accordance with the method of Example 2. The peptides were separately diluted to 20 micrograms/ml in 0.1M $NaHCO_3$, pH 9.6. Fifty microliters of the solution were delivered to wells of polyvinyl chloride flexible microtiter plates (Dynatech Laboratories, Inc., Alexandria, Va.). After incubation overnight at 4° C., the wells were washed three tims with buffer containing Tween 20 (Biorad Laboratories, Richmond, Calif.), treated with 1% bovine serum albumin (BSA) in PBS for two hours at 4° C. and washed. Subsequently, 25 microliters of serial dilutions of the appropriate rabbit anti-sporozoite antiserum (from Example 3), were delivered to the wells, and the plate was incubated for 2 hours at 4° C. After washing, the well were incubated for 2 hours with $5 \times 10^4$ cpm in 30 microliters of $^{125}I$-labelled affinity-purified goat anti-rabbit IgG diluted in PBS containing 1% BSA. The wells were washed, cut and counted. As negative controls, peptide-coated wells were incubated with normal rabbit serum and treated as above. The results show that the rabbit anti-sporozoite antiserum contained antibodies directed against the 2× repeat and the N2 and C2 peptides (the counts obtained in control wells incubated with dilutions of normal rabbit serum are subtracted from the counts obtained in experimental wells). The results show that the antiserum recognizes four peptides, N2, C2, "charged" and "2× repeat," but not C1.

The specificity of the reaction was evaluated by inhibition assays. A constant dilution of the anti-sporozoite antiserum was incubated with serial dilutions of homologous peptides prior to delivering to the wells of the microtiter plates and this was followed, as above, by treatment of the wells with $^{125}I$-labelled goat anti-rabbit IgG. The results show that the rabbit anti-sporozoite antiserum specifically recognizes the N2, "charged", "2× repeat" and C2 peptides. Most of the reactivity of this antiserum was directed against the repetitive epitope and the C2 peptides, while titers of antibodies against the N2 peptide were rather low. The binding was specific since it was inhibited only by the homologous peptides.

EXAMPLE 5: IMMUNOBLOTTING

To rule out the possibility that the recognition of the peptides by anti-sporozoite antibodies could be the product of spurious cross reactions with irrelevant antigens present in the sporozoite preparation, the affinity-purified anti-$C_2$ anti-peptide antibodies were assayed by Western blotting against sporozoite extracts. The results show that these antibodies recognize both the intracellular precursor and the membrane-associated CS protein. Immunoradiometric assays of anti-C2 against the repeat peptide were negative, indicating that contaminant antibodies were not present.

Western blotting was performed as follows: Sporozoite extracts ($10^5$/ml.) were subjected to electrophoresis in a 10% sodium dodecylsulfate polyacrylamide gel. The separated proteins were electrophoretically transferred to nitrocellulose sheets (as disclosed by Towbin, H., et al., Electrophoretic Transfer of Proteins From Polyacrylamide Gels to Nitrocellulose Sheets: Procedure and Some Applications, Proc. Natl. Acad. Sci. (USA) 76: 4350-4354 (1979)). The nitrocellulose paper was saturated with PBS containing 5% BSA and normal goat serum for one hour at 37° C. The various lanes were cut and each lane was incubated with a different affinity-purified anti-peptide antibody. Antibodies against "2× repeat", "charged", and C2 peptides were used. Antiserum against whole sporozoite was used as a control. After extensive washing with PBS containing 1% BSA, the strips were incubated for 2 hours at room temperature with affinity-purified $^{125}$I-labelled goat anti-rabbit IgG. The strips were washed, dried, and exposed to autoradiography. Two specific bands were obtained in all cases, one corresponding to a molecular weight of 52,000 daltons (intercellular precursor of *P. knowlesi* CS protein) and one corresponding to a molecular weight of 42,000 daltons (*P. knowlesi* CS protein itself). Anti-repeat activity was only detected in the wells incubated with dilutions of the anti-sporozoite antiserum.

EXAMPLE 6: ANTIBODY ELICITATION BY THE SYNTHETIC PEPTIDES

The synthetic peptides, 2× repeat, N2, and C2, were conjugated to keyhole limpet hemocyanin using carbodiimide, according to the method of Likhite, V. et al., in Methods in Immunology and Immunochemistry. Curtis, C. A. and Chase, W. A., (Eds.), Academic Press, N.Y., 1967, pp. 150-157. The conjugates were emulsified in complete Freund's adjuvant and injected into rabbits and mice. Conjugate was injected into the footpad of rabbits (500 micrograms) and mice (100 micrograms). The animals were bled 6 weeks after immunization. The antisera were assayed against glutaraldehyde-fixed sporozoites of every species of malaria parasites by indirect immunofluorescence, as disclosed by Nardin, E. H., et al. R. Bull. WHO 57 (Suppl.): 211-217 (1979). While the antisera to the repeats were strictly species-specific, i.e. recognized only *P. knowlesi*, the antisera to N2 and C2 also reacted with *P. berghei, P. cynomolgi, P. falciparum, P. vivax, P. malariae,* and *P. brisilianum*. When incubated with *P. berghei* sporozoites, both anti-N2 and anti-C2 gave CSP reactions. This means that that they induced formation of a prominent, tail-like, precipitate at the posterior end of the parasite, as reported by Vandenberg, J., et al., Mil. Med. 154 (Supp.): 1183-1190 (1969). All reactions were specific since they were inhibited by the homologous but not by the heterologous peptide at concentrations of 50 micrograms per microliter in the incubation medium. None of the antisera reacted with sporozoites of *P. gallinaceum*.

The above results indicate that C2 and N2 are exposed on the exterior of the CS molecule and that they are accesible to interaction with antibodies. Moreover, the reactivity of anti-N2 and anti-C2 with sporozoites strongly suggests that the corresponding peptides are represented on the parasite surface, and are not removed during intracellular processing. This was confirmed by immunoblotting with extracts of *P. berghei* and *P. falciparum* sporozoites.

EXAMPLE 7: IMMUNOBLOTTING OF *P. BERGHEI* SPOROZOITES

*P. berghei* ($10^5$ sporozoites per lane) were subjected to electrophoresis on SDS-PAGE (10%) and the proteins were transferred to nitrocellulose. After saturation with 5% BSA, and incubation with 5% goat serum, the cellulose strips, were incubated with monoclonal (anti-*P. berghei*) antibodies 3D11, anti-C2, or anti-N2, washed and reincubated with a second radio-labeled antibody (affinity purified goat anti-rabbit or anti-mouse immunoglobulin). The washed strips were then subjected to autoradiography. In *P. berghei* extracts, two specific polypeptides of Mr 52,000 and 44,000 were detected by anti-N2 or anti-C2. The 44,000 Mr protein represents the processed form of the 52,000 polypeptide and is found on the surface membrane of the *P. berghei* parasite. We conclude that the surface polypeptide must contain structures, most likely at the C-terminal and N-terminal ends of the molecule, closely resembling C2 and N2, respectively.

The results of this immunoblotting experiment are shown in FIG. 2. Lanes 1 and 5 are the controls, containing mouse and rabbit serum, respectively. Lane 2 contains mouse anti-C2, lane 3 contains rabbit anti-N2 and lane 4 contains monoclonal anti-CS for *P. berghei*. Western botting with *P. falciparum* using the same methodology was also positive with anti-C2 and anti-N2.

EXAMPLE 8: PARTIAL NEUTRALIZATION OF *P. BERGHEI* SPOROZOITES BY RABBIT ANTI-N2 (*P. KNOWLESI*)

Antiserum (0.2 ml), or normal rabbit serum as a control, was incubated for 45 min at room temperature with 0.5 ml of medium 199 (Gibco, Grand Island, N.Y.) containing $3 \times 10^4$ sporozoites obtained by dissection of salivary glands of Anopheles mosquitoes. After incubation, 1 ml of medium was added and 0.2 ml ($5 \times 10^3$ sporozoites) were injected intravenously into five A/H mice, which were then examined daily for presence of the blood stage of the parasite. In four separate experiments, there was evidence of partial neutralization of the parasites by anti-N2.

Some of the mice innoculated with parasites treated with anti-N2 did not become patent. In all experimental groups the prepatent periods were longer than those of the controls. The results are shown in the following Table 1:

TABLE I

| No. of Mice Infectecd/No. of Mice Injected (Day of Patency ± SD) After Incubation of Sporozoites with: | | |
|---|---|---|
| Experiment No. | Anti-N$_2$ | Normal Serum Control |
| 1 | 0/5 | 5/5 (5.6 ± 0.4) |
| 2 | 4/5 (6.4 ± 0.4) | 5/5 (4.8 ± 0.4) |
| 3 | 5/5 (5.4 ± 0.4) | 5/5 (4.0) |
| 4 | 5/5 (5.6 ± 0.7) | 5/5 (4.4 ± 0.7) |

This increase in prepatent period is highly significant, considering that the dose response curve relating the dose of sporozoites injected to the first day of patency is quite flat, as reported by Schmidt, N.H., et al., Am. J. Trop. Med. Hyg. 31 (Suppl): 612-645 (1982).

In two other similar experiments, rabbit antiserum to C2, which had given a very strong CSP reaction (between mature infective sporozoites and antiserum) with *P. berghei* sporozoites, had no discernible effect on their infectivity for mice.

EXAMPLE 9: ALIGNMENT OF HOMOLOGOUS AREAS OF CS PROTEINS OF DIFFERENT SPOROZOITES SPECIES

The computer program ALIGN, reported by Dayhoff, M. O., et al. in Methods and Enzymology (Editors: Hirs, C. H. W. and Timasheff, S. N.) 91: 524–545 (Academic Press, N.Y., N.Y. 1983) was used to evaluate the homology between the areas containing the repeats of 3 circumsporozoite proteins: *P. knowlesi*, *P. falciparum* and *P. cynomolgi*.

The repeats of these three proteins are quite distinct (QAQGDGANAGQP for *P. knowlesi*, PNAN for *P. falciparum* and DGAAAAGGGGN for *P. cynomolgi* (the key for this notation is: A=alanine; R=arginine; D=aspartic acid; Q=glutiomine; N=asparagine; E=glutamic acid; G=glycine; I=isolucine; L=leucine; P=proline; S=serine; T=threonine; Y=tyrosine; V=valine; K=lysine; C=cysteine; M=methionine; H=histidine).

The scores were significant only for the comparison between *P. knowlesi* and *P. falciparum* repeats (4.41 SD, where a score of 3.0 indicates a probable relatedness). This accounts for the fact that certain monoclonal antibodies to the *P. knowlesi* repeats cross-react weakly with *P. falciparum*, as reported in Cochrane, et al., Proc. Natl. Acad. Sci (USA) 79: 5651 (1982).

By contrast, when the ALIGN program was used to analyze the three sequences excluding the region of the repeats, the scores were all highly significant, to wit, 23.37 S.D., 24.57 S.D. and 16.28 S.D. for comparisons between *P. knowlesi* and *P. falciparum*, *P. cynomolgi* and *P. knowlesi*, and *P. cynomolgi* and *P. falciparum*, respectively.

Figure 3:
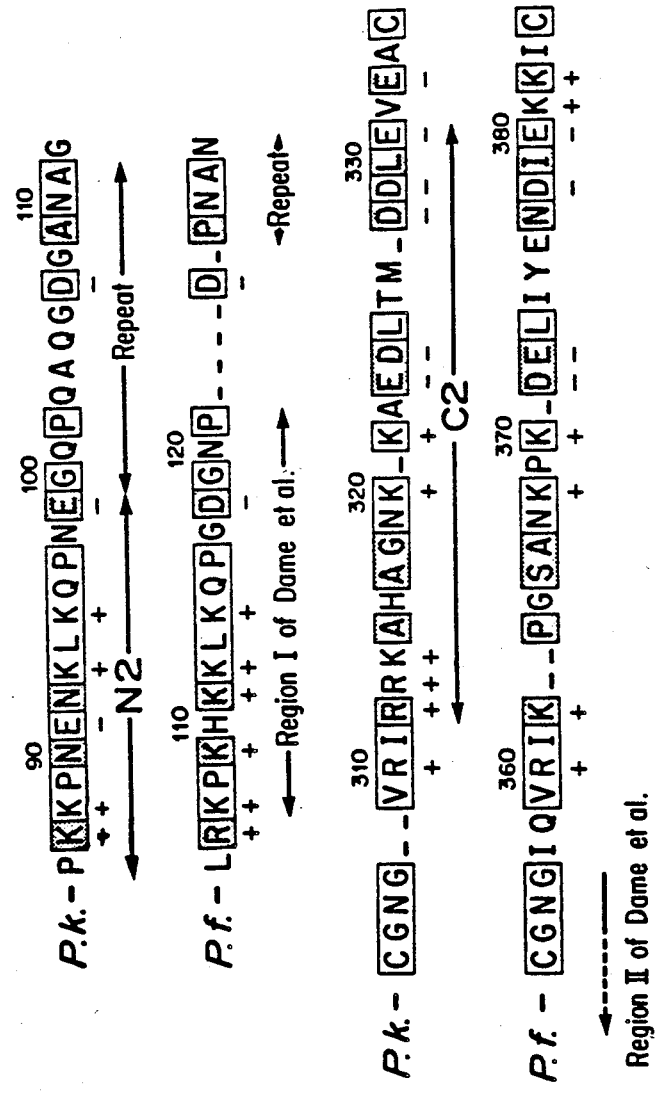
FIG. 3 is a schematic representation of segments of the *P. knowlesi* and *P. falciparum* CS protein outside the immunodominant epitope of these proteins. These segments have been aligned to achieve the highest degree of homology.

A particularly high degree of homology, most likely sufficient to preserve the tertiary structure and the functional properties of these domains, was observed between $N_2$ and $C_2$ of *P. knowlesi* with peptides in the corresponding charged areas of *P. falciparum* (see FIG. 3). These two sequences were aligned by visual inspection to achieve the maximum degree of homology. The homologous areas are indicated by white boxes in FIG. 3. The shaded boxes show residues which are known to be frequently interchanged by single-base substitutions among homologous proteins, as established by McLachlan, A. D., J. Mol. Biol. 61: 409–424 (1971).

The extensive homology of these regions, which extends to the initial amino acids of the repeat segment of *P. knowlesi*, is evidence of a high degree of inter-species conservation of the structure of this region of the CS protein. This suggests that the N-terminal end of these CS molecules may be involved in an important sporozoite function.

This alignment of the homologous regions of CS proteins of different species can be used to identify homologous peptides in CS proteins of different species. Thus, the region of the *P. falciparum* CS protein corresponding to $N_2$ of *P. knowlesi* will have the amino acid sequence: Arg-Lys-Pro-Lys-His-Lys-Lys-Leu-Lys-Gln-Pro-Gly-Asp.

Similarly, the region of the *P. falciparum* CS protein corresponding to $C_2$ will have the structure: Lys-Pro-Gly-Ser-Ala-Asn-Lys-Pro-Lys-Asp-Glu-Leu-Ile-Tyr-Glu-Asn-Asp-Ile-Glu.

Once the amino acid sequences of such peptides are known, the corresponding nucleotide sequences can be derived. DNA fragments comprising these nucleotide sequences may be used in genetic engineering constructs in conjunction with DNA fragments corresponding to their repeats, to prepare genetically engineered antigens capable of eliciting antibodies in a host with increased neutralization activity against sporozoites. This activity crosses species lines and is therefore of considerable importance as an element in the creation of a vaccine to protect mammals against malaria.

---

-- Appendix A

Text of Related Application Serial No. 99,652 Incorporated by Reference

PROTECTIVE PEPTIDE ANTIGEN

BACKGROUND OF THE INVENTION

The present invention relates to the field of antigens suitable for providing protective immunity against malaria when incorporated into a vaccine. Malaria constitutes a worldwide public health hazard of enormous economic and medical significance. The disease contributes substantially to infant mortality in endemic areas and remains a severe and debilitating illness for those who remain afflicted with it as adults. Despite advances in the techniques of mosquito abatement and improved public health measures, regions where the disease is considered endemic are increasing in area. Furthermore, the risk of infection has substantially increased in some parts of the world because of the occurrence of new drug-resistant strains of the malaria parasite.

The causative agent of malaria is a protozoan of the genus Plasmodium. Individual species within the genus appear to have a restricted host range for the animals they infect. For example, P.berghei and P.yoeli are infective to rodents, P.knowlesi and P.cynomolgi are primarily infective to monkeys, while P.falciparum, P.vivax, P. ovale nd P. malariae are the species primarily infective to humans. Despite species differences in host range, the life cycles, mode of infection, biochemistry and genetics of the various Plasmodium species are markedly similar.

The life cycle of Plasmodium is complex, the organism undergoing several distinct morphological changes, involving the participation of a mammalian host and a mosquito vector. The parasite, in the sporozoite form, is introduced to the mammalian host through the bite of the mosquito vector. The sporozoites rapidly disappear from the blood stream and are next found as intracellular parasites of liver parenchymal cells. A blood infection ensues, characterized by the well-known clinical symptoms of malaria after a complex series of morphological and biochemical transitions. The parasite is then found in the red blood cells, where it continues its development. Substantial amounts of the parasite may be obtained from the red blood cells of infected patients.

Vaccine development, to provide protective immunity against malaria infection has been thwarted by the fact that the parasite's life cycle in the mammalian host is primarily intracellular. Except for brief periods of time, the parasite is protected from contact with the immune system. Two stages in the parasite's life cycle during which it becomes briefly exposed to the immune system are, 1) the interval following initial infection before sporozoites have successfully invaded the cells of the liver and 2) the interval during which merozoites leave infected red blood cells and enter uninfected red blood cells. The transient exposure of the merozoite forms in the extracellular milieu has provided the basis for prior art attempts to develop host immunity to blood forms of the parasite. European published Patent Application, Number 62924, discloses antigenic proteins useful in the making of a vaccine to provide immunity against merozoite forms of the parasite. The utility of such a vaccine would presumably lie in limiting or arresting the course of the established maldria infection.

An alternative approach, based upon sporozoite antigens has led to the discovery of antigenic and immunogenic proteins of sporozoites that are capable of providing protective immunity against initial infection, when administered as a vaccine, Cochrane, A. H., et al., in Malaria, vol. 3, (J. Kreier, ed.) Academic Press N.Y. (1980) pp. 163-202; Nussenzweig, R. S. in Immunity to Blood Parasites of Animals and Man, (L. Miller, J. Pino and J. McKelvey, eds.) Plenum, N.Y. (1977) pp. 75-87. Gwadz, R. W., et al., Bull, W. H. O. Suppl. 1, 57, 165 (1979); Clyde, D. F., et al., Am. J. Trop, Med. and Hyg. 24, 397 (1975); McCarthy, V., et al., Exp. Parasitol. 41, 167 (1977).

These proteins are antigenically distinguishable for each Plasmodium species, but have numerous structural properties in common including chromatographic behavior, isoelectric point, and electrophoretic mobility. The sporozoite antigens range in molecular weight from approximately 40,000 daltons to 70,000 daltons and have low isoelectric points, Santoro, F. et al., J. Biol. Chem. 258, 3341, 1983.

The comparison of tryptic digests of purified sporozoite antigen proteins of different Plasmodium species shows that several tryptic peptides have identical retention times on reverse-phase high performance liquid chromatography, indicating that there is a high degree of homology between antigenic proteins of different species.

The sporozoite antigens are components of the sporozoite surface coat. The presence of the sporozoite antigens is indicated by a characteristic immunologic reaction known as the circumsporozoite reaction, and by immunofluorescence tests. See Vanderberg, J. P., et al, Mil. Med. (Suppl.) 134, 1183 (1969); and Nardin, E., et al, Nature 274, 55 (1978).

These reactions make it possible to specifically detect the sporozoite antigen for a given Plasmodium species, without resorting to time-consuming in vivo tests. This, in turn, has made it possible to develop specific radioimmunoassays for sporozoite antigens, and ultimately for the production of malaria antibodies directed against sporozoite antigens of Plasmodium species.

Antibodies against the sporozoite antigens have been shown to provide protective immunity against the Plasmodium species from which they were derived, in rodents, monkeys and in human volunteers. The sporozoite protective antigen protein is herein termed CS protein, circumsporozoite protein, or sporozoite CS protein, these terms being deemed equivalent. A co-pending U.S. application, Serial No. 234,096, filed February 12, 1981, has been filed, disclosing a vaccine based upon purified CS protein. Said application (a copy of which is annexed hereto as Appendix A) is incorporated herein by reference as though set forth in full.

The results disclosed herein are based in part on the techniques and concepts of the field of immunology. For convenience, certain terms commonly used in the art are defined herein. The term "immunochemical reaction" is used to denote the specific interaction which occurs between an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art. The terms "immunogenic" or "antigenic" will be used here to describe the capacity of a given substance to stimulate the production of antibodies specifically immunoreactive to that substance when that substance is administered to a suitable test animal under conditions known to elicit antibody production. The term "protective antigen" refers to the ability of a given immunogen to confer resistance in a suitable host, against a given pathogen. The term "epitope", refers to a specific antibody binding site on an antigen. Macromolecular antigens such as proteins typically have several epitopes with distinctive antibody binding specificities. Different epitopes of the same antigen are distinguishable with the aid of monoclonal antibodies which, due to their high degree of specificity, are directed against single epitopes. Two different monoclonal antibodies directed against different epitopes on the same antigen may each bind the antigen without interfering with the other, unless the epitopes are so close together that the binding of one sterically inhibits the binding of the other. The term "immunodominant region" denotes an area of the antigen molecule which is mainly responsible for its antigenicity.

SUMMARY OF THE INVENTION

The present invention is based on the discovery that the protective CS sporozoite antigens of the genus Plasmodium possess a single immunodominant region composed of repetitions of the same epitope. For P.knowlesi, the epitope has,been shown to be a dodecapeptide whose sequence is repeated several times within the structure of the CS protein. The repeated peptide has been chemically synthesized in both monomeric and dimeric forms. The synthetic repeated peptide is immunochemically reactive with polyclonal antibody preparations against P.knowlesi. In addition, all monoclonal antibodies against CS proteins which neutralize the infectivity of sporozoites in vitro, also react with the synthetic peptide. Therefore, the synthetic repeated peptide constitutes substantially all of the immunogenic activity displayed by the naturally occurring sporozoite protective antigen of P.knowlesi.

Several lines of evidence indicate that CS proteins of the Plasmodium species infective to rodents, monkeys and humans are structurally similar. All possess an immunodominant region composed of similarly repeated epitopes. For each species, the repeated peptide of the sporozoite CS protein can be synthesized. The repeated peptide of a CS protein is immunogenic when administered in a composition, and by administration methods, known in the art to yield antibody production. On the basis of the discoveries and teachings herein described, structural determination and synthesis of the repeated peptide corresponding to any Plasmodium species sporozoite, and the preparation of a vaccine composition incorporating said peptide and capable of eliciting protective immunity against said species is now available to those of ordinary skill in the art.

As further confirmation of the close relationship of CS proteins of different Plasmodium species, monoclonal antibodies against P.knowlesi sporozoites have been shown to cross-react with P.falciparum antigen, a species infective to humans. It is therefore apparent that the development of other synthetic peptides more specifically reactive with human malaria species are well within the grasp of those ordinarily skilled in the art, following the teachings and disclosures as set forth herein.

DETAILED DESCRIPTION OF THE INVENTION

In the following description, the materials employed were commercially available, unless otherwise specified. Enzymes used in the cloning procedures were obtained from commercial sources. Restriction endonuclease reactions were carried out according to the manufacturer's instructions. Unless otherwise specified, the reaction conditions for other enzyme reactions were standard conditions used in the art, as described, for example, in Methods in Enzymology, volume 60 (R. Wu, Ed.) Academic Press, (1980). Unless otherwise specified, the abbreviations herein are standard abbreviations acceptable for publication in scientific journals normally used by those skilled in the art to publish their results, such as those cited herein.

In general outline, the experiments and conclusions following from the results thereof are set forth. The approach taken herein to clone a DNA segment coding for the sporozoite antigen protein was to clone cDNA made from mRNA obtained from infected mosquitoes. The cDNA approach was preferred in the initial cloning work because it was not known whether Plasmodium genomic DNA contained introns that might prevent the expression of antigenically identifiable sporozoite proteins. Now that the short and repeated nature of the epitope is known, it is feasible to select for DNA encoding the epitopes from a library of genomic Plasmodium DNA. The initial experiments were performed with cDNA from mRNA of infected mosquitoes, since it was only at that stage that the Plasmodium was known to express the sporozoite antigen. A cDNA library was constructed from Poly (A)$^+$RNA derived from P.knowlesi-infected mosquitoes. Double stranded cDNA, tailed with poly-C residues, were inserted into the plasmid pBR322, previously cut with Pst I and tailed with poly-G. Host cells transformed to tetracycline resistance were selected and single colonies of transformed cells were stored in microtiter dishes at -70°C.

The cDNA clones were screened for the ability to express a protein that contained the immunochemically reactive region of the sporozoite surface antigen. Once a cDNA coding for the sporozoite antigen was identified, others could readily be detected by hybridization using the originally cloned cDNA as a probe. Clones derived either from cDNA or genomic DNA libraries could be identified in this manner, based upon the homology between DNA segments coding for the sporozoite antigen of different Plasmodium species. Identification of clones expressing an immunoreactive protein was done by screening lysates of colonies of cells transformed (as above) with the cloned cDNA. Pools of 48 colonies were screened using a sensitive, two-site immunoradiometric assay performed with monoclonal antibodies. This permitted the detection of the CS protein in the transformed cells.

In short, a monoclonal antibody to P.knowlesi CS protein was adsorbed to the wells of a microtiter plate. Lysates from pools of 48 colonies were each added to the wells and incubated for sufficient time to allow the immunoreactive protein present in the lysate to bind to the adsorbed monoclonal antibody. The wells were then washed to remove any contaminating protein and a radio-labelled second monoclonal antibody to P.knowlesi CS protein was added. The labelled second monoclonal antibody attaches to the antigenic protein that is already bound to the surface of the microtitre well by the first monoclonal antibody. If a pool of 48 colonies was found to be positive, the colonies were screened individually in the same fashion. In this manner, positive clones were identified.

Whenever an immunoreactive clone was detected, plasmid DNA was isolated from it and used to transform another host cell strain, such as E.coli HB 101 or E.coli RR1. Transformants detected by tetracycline resistance were rechecked for the ability to express the immunochemically reactive protein, in order to confirm that the expression was a property of the plasmid DNA clone containing CS nucleotide sequences. Once suitable plasmid DNA was obtained from the positive clones, the nucleotide sequence of the cDNA insert coding for at least the immunoreactive region of the CS protein was obtained (by cloning onto M13). Methods of nucleotide sequence analysis are well known in the art, including the method of Maxam and Gilbert, W. Proc. Nat. Acad. Sci. USA 74, 560 (1977) and the method of Sanger, F. et al, Proc. Nat. Acad. Sci. USA 74, 5463 (1977). The latter method was employed in the present work. The complete nucleotide sequence of a segment of the P.knowlesi CS protein gene that contains the immunochemically reactive site is shown in Figure 1.

A surprising feature of the nucleotide sequence was that it was repetitive. In P. knowlesi the sequence consisted of a 36 base pair repeat, 8 complete units of which were represented in one clone (24-mer) together with partial units at either end. In order to deduce the amino acid sequence coded by the DNA, it was necessary to identify the coding strand and, within the strand, the correct reading frame. In this context, the advantage of using the Sanger and Coulson, supra sequencing method becomes evident. A sequencing vector, bacteriophage M13mp9, contains a betagalactosidase gene with a Pst I site in the same reading frame as the Pst I cleavage site of pBR322. Therefore, the reading frame can be deduced once the number of deoxy C-residues added during the tailing reaction is known and the sequencing vector can express a beta-galactosidase fusion protein comprising the immunochemically reactive part of the CS protein. Therefore, two different M13mp9 recombinants were obtained, with the 368 bp P.knowlesi DNA fragment inserted in opposite orientations. Only one of the two recombinants produced immunochemically reactive betagalactosidase fusion protein, as measured by the above-described radioimmunoassays. The clone producing the immunoreactive protein was used to identify the coding strand and direction of transcription of the P.knowlesi gene fragment.

The correct reading frame was also deduced using immunological procedures. These showed that the epitope defined by the monoclonal antibodies was destroyed by elastase, but not by trypsin nor by reducing agents, indicating that the epitope did not contain any of lysine, arginine or disulfide bonds, but might contain alanine residues.

On the basis of such experiments, the amino acid sequence of the 12 amino acid-containing repetitive peptide was deduced to be:

$H_2N$-GlnAlaGlnGlyAspGlyAlaAsnAlaGlyGlnPro-COOH.

To confirm the deduced amino acid sequence and immunochemical reactivity of the above-described sequence, a dodecapeptide of the same amino acid sequence and a dimer thereof were synthesized using an automated solid phase peptide synthesis system.

The monomer and dimer synthetic peptides were separately tested for immunochemical activity in the same type of radioimmunoassay as was used initially to screen the cDNA library. In this test, two antibody binding sites must be present in the antigen, one for binding to the first monoclonal attached to the microtiter well and the second for binding the added labelled antibody. Although the monomer peptide did not bind the labeled antibody, the dimer peptide was reactive, indicating that the dimer contained two complete, or nearly complete, antibody binding sites. Furthermore, the same assay showed that the monomer was able to compete with and specifically inhibit the binding of CS proteins of P.knowlesi to the microtiter wells bearing the first monoclonal antibody. Therefore, the sequence shown above contains an epitope of the sporozoite antigen. Another important observation was that all monoclonal antibodies to P.knowlesi obtained to date, as well as all polyclonal antibodies obtained from monkeys immunized with irradiated sporozoites, also reacted with the synthetic peptides. Actually, more than 70% of the antibodies to sporozoites, found in the serum of the immunized monkeys, recognized this single epitope (Zavala, et al., J. Exp. Med. 157:1947, 1983).

Therefore a chemically synthesized dodecapeptide having an amino acid sequence identical to that repeated in a sporozoite membrane protein contains substantially all of the antigenicity of the naturally occurring CS protein. It follows that based upon the principles of immunology and following techniques and procedures known to those of ordinary skill in the art, a synthetic peptide based upon the known amino acid sequence of a sporozoite CS protein can be incorporated into a vaccine composition capable of providing protective immunity in a host organism susceptible to a Plasmodium species from which the sequence of the peptide was derived. The following experiments, generally described, demonstrate the essential structural and functional similarities between the sporozoite CS proteins of the Plasmodium species infective to rodents, monkeys and humans. These similarities are exploitable to identify and synthesize the antigenic peptides specific for any Plasmodium species including, in particular, those infective to humans. The structural determination and synthesis of the repeated peptide for any Plasmodium species can be carried out by methods described herein or by equivalent methods known in the art, or by methods known in the art which exploit the disclosures and teachings of the present invention to eliminate some of the more time-consuming and tedious aspects of the original experiments. Of significance is that cross reactivity has been observed between monoclonal antibodies to the CS proteins of different Plasmodium species. For example, antibodies to the CS protein of P.knowlesi cross react with the CS protein of P.cynomolgi and P.falciparum; antibodies to the CS protein of P.cynomolgi cross react with the sporozoite antigen of P.vivax; antibodies to the CS protein of P.yoeli nigeriensis cross react with sporozoite antigen of P.berghei, and in that instance, completely neutralize the infectivity of sporozoites of the latter species, for mice.

Additional immunochemical evidence has been adduced to demonstrate that all sporozoite CS proteins have a single immunodominant region and repetitive epitopes Zavala, et al., supra. The binding of several different monoclonal antibodies directed against the same sporozoite CS protein was tested, measuring the inhibitory effects that the binding of one might have on the other. Monoclonal antibodies directed against different sequences within an antigen should not interfere with their respective binding capacities. Conversely, if monoclonals are directed against the same epitope, or epitopes which are topographically close, they inhibit each other. In the case of P.knowlesi, every one of the six monoclonals used, strongly inhibited the binding of the others to the antigen.

The same experiments were performed using monoclonals to the sporozoite antigen proteins of P.vivax, P.falciparum, P.malariae P.cynomolgi and P.berghei, with identical results. Therefore, these sporozoite CS proteins all are characterized by having a single immunodominant region.

Of direct relevance to the development of a vaccine against human malaria is the observation that antibodies in the serum of humans vaccinated and protected against sporozoites of P.falciparum or P.vivax are also directed against the same immunodominant region of the sporozoite CS protein. Pretreatment of a crude extract of sporozoites of either species with a single monoclonal antibody directed against the sporozoite antigen of the same species almost completely inhibited the subsequent binding of the antigen (in the sporozoite extract) to polyclonal antibodies isolated from the serum of the vaccinated human volunteers (Zavala, et al., supra).

The fact that immunodominant regions of the CS proteins contain repetitive epitopes was demonstrated by a solid phase two site radioimmunoassay. In the assay, a monoclonal antibody was bound to the plastic surface a microtiter well, antigen was added and the antigen was found to the immobilized antibody. The well was then washed to remove any unbound material and a second monoclonal antibody, presumably directed against a different epitope of the same antigen, was added. The second antibody is labelled with a radioisotope to quantitate the binding of the second antibody. Binding of the second antibody is proportional to the amount of antigen bound in the well. This immunoassay can be performed only if the antigen contains at least two epitopes. The first epitope binds to the antibody immobilized to the plastic of the plate, the second binds the radiolabelled antibody. Surprisingly, in the case of every CS protein, the two site radioimmunoassay could be performed using a single monoclonal antibody. That is to say, the assay could be performed using unlabelled monoclonal antibody A as the first monoclonal and the same monoclonal A as the second monoclonal. The result demonstrates that the sporozoite CS protein has at least two identical epitopes.

A control experiment demonstrated that the result was not an artifact caused by aggregation of the sporozoite antigen protein. Extracts of P.knowlesi sporozoites were dissolved in 2.0% (w/v) sodium dodecylsulfate and 6M urea and fractionated by ultracentrifugation in sucrose gradients. The existence of two epitopes was demonstrated in fractions of the gradient containing proteins of molecular weight 40,000, corresponding to the size of a CS protein monomer. Furthermore, there was no indication of the presence of aggregates of CS proteins. Identical results were obtained in experiments performed with P.vivax and P.falciparum extracts (Zavala, et al, supra).

It is therefore clear that all sporozoite CS proteins have a single immunodominant region comprising a peptide repeated many times within the protein. The repeated peptide contains the epitope, and each sporozoite CS protein is composed of a plurality of such repeated peptide epitopes. These epitopes are very immunogenic in all animal species, including man. Synthetic peptides containing the epitope of a given sporozoite CS protein are functionally identical to naturally occurring sporozoite antigens, with the obvious exception of two site radioimmunoassays requiring two epitopes on the same molecule. The functional behavior in two site assays is reproduced by synthetic dimers of the repeated peptide.

It will be readily appreciated therefore that synthetic peptides, comprising an amino acid sequence corresponding to an epitope of a sporozoite CS protein in monomeric or multimeric form, can be incorporated into vaccines capable of inducing protective immunity against sporozoites of malaria parasites, e.g., P.falciparum, P.vivax and P. malariae. Techniques for enhancing the antigenicity of such repeated peptides include incorporation into a multimeric structure, binding to a highly immunogenic protein carrier, for example, keyhole limpet hemocyanin, or diptheria toxoid, and administration in combination with adjuvants or any other enhancers of immune response. Furthermore, it will be understood that peptides specific for a plurality of Plasmodium stages and species may be incorporated in the same vaccine composition to provide a multivalent vaccine. In addition, the vaccine composition may comprise antigens to provide immunity against other diseases in addition to malaria.

An amino acid sequence corresponding to an epitope of a CS protein (repeated peptide) may be obtained by chemical synthetic means or by purification from biological sources including genetically modified microorganisms or their culture media. The repeated peptide may be combined in an amino acid sequence with other peptides including fragments of other proteins, as for example, when synthesized as a fusion protein, or linked to other antigenic or non-antigenic peptides of synthetic or biological origin. The term "corresponding to an epitope of a CS protein" will be understood to include the practical possibility that, in some instances, amino acid sequence variations of a naturally occurring repeated peptide may be antigenic and confer protective immunity against malaria sporozoite infection. Possible sequence variations include, without limitation, amino acid substitutions, extensions, deletions, interpolations and combinations thereof. Such variations fall within the contemplated scope of the invention provided the peptide containing them is antigenic and antibodies elicited by such peptide cross-react with naturally occurring CS protein or non-variant repeated peptides of CS protein, to an extent sufficient to provide protective immunity when administered as a vaccine. Such vaccine compositions will be combined with a physiologically acceptable medium. Routes of administration, antigen dose, number and frequency of injections are all matters of optimization within the scope of ordinary skill in the art, particularly in view of the fact that there is experience in the art in providing protective immunity by the injection of inactivated sporozoites. It is anticipated that the principal value of providing immunity to sporozoite infection will be for those individuals who have had no previous exposure to malaria, e.g., infants and children who live in endemic and subendemic areas, and unexposed adults travelling into endemic areas. It is also anticipated that temporary immunity for infants may be provided by immunization of mothers during pregnancy. Details of the operation and practice of the present invention are set forth in the specific examples which follow.

EXAMPLE 1 cDNA clone coding for a sporozoite antigen protein.

The techniques of recombinant DNA technology make extensive use of enzyme-catalyzed reactions. Purified enzymes for use in the practice of the present invention are currently available from commercial sources. Commercially available enzymes and reagents were employed unless otherwise specified. Restriction endonucleases, their nomenclature and site specificities, have been described in detail by Roberts, R.J., Nucl. Acids Res., 8, p. 63 (1980). The restriction enzymes used in this work were used in amounts and under reaction conditions specified by the manufacturer for each enzyme.

Approximately 1000 P.knowlesi infected mosquitoes grown, maintained and collected as described by Cochrane et al., Proc. Natl. Acad. Sci. USA 79:5651-5655 (1982) were harvested and dissected to obtain thoracic segments which were stored on ice until the dissection was completed. RNA was prepared from the thoraxes essentially as described by Seeburg, P.H., et al; Cell, 12, 157 (1977), and by Chirgwin, J. M., et al; Biochemistry, 24, 5294 (1979). The tissue was homogenized in 10ml of 5M guanidine thiocyanate, pH 5.0, 10mM EDTA and 0.1M 2-mercaptoethanol until all the tissue was dispersed. The solution was centrifuged at 10,000 rpm for 10 minutes and the supernatant adjusted to 2% (w/v) Sarkosyl (Trademark, ICN Pharmaceuticals, Plainview, New York), and heated at 65°C for two minutes. Cesium chloride was then added (0.1g/ml of solution) and the resulting solution was layered over 2ml cushions of half-saturated CsCl in 10mM EDTA in SW41 (Trademark, Beckman Instruments, Fullerton, Calif.) cellulose nitrate tubes. Centrifugation was at 28,000 rpm for approximately 20 hours at 20°C. The RNA pellet was dissolved in 5mM EDTA, 0.5% (w/v) Sarkosyl and 5% (w/v) 2-mercaptoethanol, extracted with phenol and chloroform and precipitated with ethanol. Usually, 0.5-1 mg of RNA were obtained per g of tissue. The RNA was then passed over an oligo (dT)-cellulose column (Aviv, H., et al, Proc. Nat. Acad. Sci. USA, 69, 1408 (1972), to enrich for the polyadenylated fraction. Alternatively, the RNA can be prepared from the mosquito thoraces by the procedure modified from Liu, C.P., et al., Proc. Nat. Acad. Sci. 76:4503, 1979. According to this procedure, tissue was homogenized in 8-10 vol. of 4M guanidine isothiocyanate pH 5.0 (with glacial acetic acid) and 0.1 M 2-mercaptoethanol until the tissue was dispersed. Centrifugation took place at 9,000 rpm for 3 minutes, and the supernatant was layered over 0.2 vol. of 5.7M CsCl in 0.10M EDTA (pH 6.5) in SW 41 cellulose nitrate tubes. Centrifugation was at 35,000 rpm for 16-20 hours @ 20°C. Approximately 0.5-1 mg of RNA was obtained per gram of tissue. Poly(A)+RNA was then oligo-dT selected as described above.

A sample of mRNA isolated as described was translated in vitro using a translation system prepared from wheat germ (modified from Roberts, B.E., et al, Proc. Nat. Acad. Sci. USA, 70, 2330 (1973)). Proteins produced by in vitro translation were immunoprecipitated as described in Example 2, (alternatively, as disclosed by Goldman, B.M., and Blobel, G., Proc. Natl. Acad. Sci., 75:5066 (1978)) and fractionated on an SDS-polyacrylamide gel (SDS-Page) as described by Yoshida, et al, J. Exp. Med 154, 1225 (1981) and in Example 2 of copending U.S. application Ser. No. 234,096, incorporated herein by reference. mRNA fractions containing sequences coding for the CS-proteins can be identified by this means.

For preparative cDNA synthesis total polyadenylated mRNA (approximately 20 $\mu$g) was treated in 100 $\mu$l volume with 1mM methyl mercury (hereinafter MeHg) (Aldrich Chemical, Milwaukee, Wisconsin) at room temperature for 5 minutes. The treatment was stopped by adding 0.5% (0.5 $\mu$l per 100 $\mu$l) of undiluted $\beta$-mercaptoethanol and incubating at room temperature for 5 minutes. The MeHg treated polyadenylated mRNA was incubated in 200 ul reaction containing 50mM Tris-HCl pH 8.3, 10mM $MgCl_2$, 20mM KCl, 5mM Dithiothreitol, 2mM each of dATP, dCTP, dGTP and dTTP, 50 $\mu$Ci $^{32}$PdCTP (specific activity, 800 Ci/mmol), 4 $\mu$g oligo(dT)12-18, (Collaborative Research, Waltham, Massachusetts) 5 μl RNasin (BIOTECH, Madison, Wisconsin) and approximately 200 units reverse transcriptase (from Beard, Life Sci., St. Petersburg, Fla.). Incubation was at 42° for 60 minutes.

The reaction was stopped by extraction with phenol and chloroform (1:1), then with an equal volume of chloroform and precipitation by ethanol. The ethanol precipitate was dissolved in 50 μl 10mM Tris-HCl, 1mM EDTA, pH=8 and fractionated on a column of Sephadex (Trademark, Pharmacia, Inc., Uppsala, Sweden) G-75 in a 1ml Falcon (Trademark, Falcon Plastics, Oxnard, California) plastic pipette, using 10mM Tris-HCl, pH 7.4, and 1mM EDTA as the running buffer. The leading peak of unexcluded $^{32}$P counts was collected (approximately 300 μl) and adjusted to 0.3M NaOH and 1mM EDTA and incubated overnight at room temperature. Following neutralization with 5M sodium acetate pH 3.8 to a final pH of approximately 6.0, and ethanol precipitation, the second DNA strand was synthesized in a 50 μl reaction containing the same buffer as described supra, 500 μM each of dATP, dCTP, dGTP, dTTP, 125 μCi $^{32}$PdCTP (800Ci/mmole) and 50 units reverse transcriptase. Incubation was at 37°C for 90 minutes. The reaction products were extracted with phenol/chloroform and passed over a Sephadex G-75 column as described above and the excluded $^{32}$P peak was precipitated with ethanol before proceeding to treatment with $S_1$ nuclease.

After fractionation on Sephadex G-75, the second cDNA strand synthesis was completed using the Klenow fragment of DNA polymerase I (Boehringer-Mannheim) in the presence of 50mM Tris-HCl, pH 8.0, 7mM $MgCl_2$ and 1mM dithiothreitol. The reaction mixture was incubated for 4 hours at 15°C, extracted with phenol-chloroform (1:1) and precipitated with ethanol as described above.

The double stranded cDNA was incubated with 300 units of S1 nuclease (Boehringer-Mannheim, Indianapolis, Indiana) in 24 μl of 0.3mM NaCl, 30mM Na acetate, pH 4.5, and 3mM $ZnCl_2$ at 41°C for 5 minutes. The reaction was stopped by the addition of EDTA to 10mM and neutralized with Tris base. The $^{32}$P-labelled cDNA was size fractionated using a column of Sepharose CL-4B (Trademark, Pharmacia, Inc., Uppsala, Sweden) made up in a 1ml Falcon plastic pipette and run in a buffer of 0.3M NaCl, 10mM Tris-HCl pH 8.0, 1mM EDTA. Various size classes of double-stranded cDNA were precipitated with ethanol and then tailed using calf thymus terminal transferase (Enzo Biochem., Inc., New York, New York) in a 100 μl volume for 1 minute at 37°C in a buffer containing 100mM K cacodylate, pH 7.6, 1mM $CoCl_2$, 0.1mM DTT, 0.1mM dCTP, 4 μCi of $^3H$-dCTP, 24Ci/mmole), and approximately 20 units terminal transferase/μm ds-cDNA. The reaction was stopped by adjusting the solution to 0.5M NaCl, 10mM EDTA and incubating at 65°C for 5 min. 1-5 micrograms of yeast + RNA were added prior to extraction with phenol: chloroform and precipitated with ethanol twice. The tailing reaction is described, generally, by Roychoudhury, R., et al, Nucl. Acids Res., 3, 101 (1976). An alternative procedure, also conducted, is described by Land, H., et al, Nucl. Acids. Res. 9:2251, 1981. Approximately 17 bases were added to the 3' end under these conditions. Plasmid pBR322 cleaved by Pst I endonuclease and tailed with dG residues was obtained from a commercial source, New England Nuclear, Boston, Massachusetts. Equimolar amounts of dC tailed cDNA and dG tailed pBR322 were annealed at a concentration of 1 μg/ml, using sequential 2 hour incubations at 42°C, 30°C, and 14°C. The hybrid plasmid DNA was ethanol-precipitated and then used to transform E.coli RR1 cells to ampicillin resistance. Libraries of single colonies were generated and stored in microtiter dishes at -70°C.

According to the alternative procedure, after 15-30 deoxy C residues have been added to the cDNA and annealing to an equimolar concentration of dG-tailed pBR 322 has taken place (at 250ng of vector/ml), the annealing mixture was incubated at 68°C for 5 min, then at 42°C for two hours, followed by slow cooling to room temperature for 2 hours. The hybrid plasmid DNA was used to transform E.coli RR1 cells to tet-resistance as described by Dagert, M. et al, Gene 6:23, 1979. A library was generated and stored as individual colonies in Luria broth with 15% glycerol in microtiter dishes at -70°C.

A library of (300-2000bp) cDNA fragments was screened for colonies that expressed protein containing the immunochemically reactive region of the sporozoite surface antigen protein. Forty-eight colonies were grown individually on a petri dish containing S agar (32g/litre tryptone, 5g/litre NaCl, 20g/litre yeast extract, 15g/litre Difco agar 0.2g/litre NaOH and 20mg/liter tetraclycline). The plates were flooded with 2mls of 0.05M Tris-HCl pH 7.5 and 0.5mg egg-white lysozyme (Sigma, St. Louis, Mo.) and scraped with a sterile spatula into a 15ml polypropylene tube (Fisher Scientific Supply). After incubation at room temperature for 30 minutes, followed by 60 minutes on ice freeze thawing in 95% ethanol and dry ice (-80°C) three times, and further incubation at 37°C for 10 minutes the crude cell extracts were treated with DNAse I (1mg/ml), 4mM $CaCl_2$ and 4mM $MgCl_2$ at room temperature for 30 minutes and stored at -70°C for future use.

The lysates were screened for the presence of any immunochemically reactive protein using P.knowlesi monoclonal antibodies, in a radioimmunoassay. In this method, anti-P.knowlesi monoclonal antibody adsorbed to the well of a microtiter dish was used to affinity purify any immunoreactive protein present in pooled cell lysate. Lysates containing an immunoreactive protein were detected by reacting the washed microtiter wells with a second $^{125}I$-labelled anti-P.knowlesi monoclonal antibody. To do this, microtiter plates were coated with 50µl anti P.knowlesi monoclonal antibody (50 µg/ml) incubated at 4°C for 12-17 hours, washed thoroughly with 1% (w/v) BSA-saline solution, and then incubated with 50 ul of the pooled cell extract for 4-17 hours at 4°C. After washing, a second $^{125}I$-labelled anti-P.knowlesi monoclonal antibody was added to each well and incubated 2 hours at room temperature. The washed wells were then tested individually for radioactivity. When a pool of 48 colonies was found to be positive, the original single colonies that made up the pool were screened individually and the immunoreactive clones identified, isolated and genetically purified.

Plasmid DNA was purified from 1 litre of cells containing an immunoreactive clone (plasmid pEG81). The cells were grown at 37° in Luria broth with 15µg/ml tetracycline to approximately $5 \times 10^8$/cells per ml and the plasmid DNA amplified by adding 175 µg/ml of chloramphenicol and incubating overnight (Clewell and Helinski, J. Bacteriol. 110, 1135 (1972)). The plasmid DNA was extracted from the cells using sodium dodecyl sulphate (SDS) (Godson and Vapnek, Biochim. Biophys. Acta 299, 516 (1973) and purified using 5-20% (w/v) sucrose density gradients. This yielded 500-1000 μg plasmid RF I DNA. 1 μg of this was used to transform other E.coli cells (HB101) to tetracycline resistance and their ability to express the immunoreactive protein was re-checked.

pEG81 DNA was digested with Pst I restriction endonuclease ligated with T4 DNA ligase to 0.5 μg of Pst I-cut cloning/sequencing vector M13mp9 at a 1:1 molar ratio and sequenced using the Sanger dideoxy chain termination method (Sanger and Coulson, supra) with a "universal" synthetic primer 5' - d[GTAAAACGACGGCCAGT] - 3' (purchased from PL Biochemicals, Milwaukee, Wisc.). The complete nucleotide sequence of this segment of the P.knowlesi CS protein gene that contains the immunoreactive site is shown in Figure 1.

An unexpected feature of the pEG81 fragment of P.knowlesi DNA is that it consisted entirely of a 36 base pair repeat (8 complete units plus a partial unit on either end). The coding strand and correct reading frame of the nucleotide sequence was established as follows:

(a) The reading frame of the Pst I cleavage site of pBR322 ampicillinase gene and of the M13mp9 β-galactosidase genes are known to be identical (5' X C T G C A G X X 3').

|        | Met | Thr | Met | Ile | Thr | Pro | Ser | Leu | Ala | Ala | Gly |
|--------|-----|-----|-----|-----|-----|-----|-----|-----|-----|-----|-----|
| M13mp9 | ATG | ACC | ATG | ATT | ACG | CCA | AGC | TTG | GCT | GCA | GGT |

Pst I Cleaving Site

Two different M13mp9 recombinants were obtained with the P.knowlesi DNA fragment inserted in opposite orientations. One of the recombinants produced an immunoreactive -galactosidase fusion protein (M13mp9/Pk 11) as measured by the radioimmunoassay described supra, the other clone did not. The sequence of M13mp9/Pk 11 therefore identified the coding strand of the DNA.

(b) The reading frame was also deduced from the fact that 17 dC residues were inserted between the β-gal gene and the P.knowlesi gene fragment.

(c) One possible reading frame coded for an alanine-rich peptide. That the epitope probably contained alanine was verified by treating authentic P.knowlesi CS surface protein with porcine elastase, known to cleave peptides at alanine residues (Powers, J. C., et al, Biochem, Biophys. Acta, 485: 156-166, (1977). Incubation of an extract of $10^6$ sporozoites with 0.002 units porcine elastase (Worthington Enzymes, infra) in Tris-buffer, 0.05M pH 8.6, for 60 minutes at 37°C, completely abrogated the reactivity of the CS protein with monoclonal antibodies as determined by a two-site immunoradiometric assay described in Example 4. Inactivation of the CS protein by elastase was reversed by the synthetic inhibitor OOC-Ala Ala Pro Ala (Powers, et al supra).

Other possible reading frames coded for peptides which were excluded for various reasons: they were too hydrophobic or they contained several cysteine, lysine and arginine residues. The absence of such amino acid residues had been determined in experiments showing that the epitope was resistant to trypsin after complete reduction of the CS protein. Indeed, after incubation of another aliquot of the same sporozoite extract with 1mg of TPCK-trypsin (Worthington Enzymes, Freehold, New Jersey) at 37°C for 30 minutes, followed by complete reduction and alkylation, the CS protein reacted fully with the monoclonal antibodies.

The deduced amino acid sequence of the twelve amino acid repeat is as follows based upon translation of the nucleotide sequence in the correct reading frame:

Gln-Ala-Gln-Gly-Asp-Gly-Ala-Asn-Ala-Gly-Gln-Pro (All sequences are expressed from the end nearest $NH_2$ - terminus on the left to the end nearest the -COOH terminus on the right.)
The immunoreactive portion of the P.knowlesi protein is therefore contained within the 12 amino acid repeat.

To confirm that the foregoing amino acid sequence contains the immunoreactive site, a dodecapeptide (with the same order of amino acids as shown above) and a dimer of the dodecapeptide have been synthesized, using solid phase resin synthesis (Marglin, H. and Merrifield, R. B., Ann. Rev. Biochem. 39:841-866 (1970). Sequence analysis performed by automated Edman degradation confirmed that the peptide had been correctly synthesized. The final proof that this is the correct epitope has been obtained.

Rabbits were immunized with the dodecapeptide coupled to a carrier (bovine gamma globulin in complete Freunds adjuvant). Two weeks after the injection, the rabbits were bled and their serum assayed for the presence of antibodies against the dodecapeptide and against extracts of sporozoites. The results showed that the animals produced high titers (greater than 1:1000) of antibodies to the native CS protein present in the parasite extracts.

Once a clone expressing an immunochemically reactive protein has been identified, the inserted cDNA sequence can be employed as a hybridization probe to identify cDNA coding for sporozoite antigen proteins from other Plasmodium species. The cDNA clone can also be used to screen Plasmodium genomic DNA obtained, for example, from merozoites, to detect DNA sequences coding for sporozoite antigen protein. Therefore, once the first cDNA sequence coding for a sporozoite antigen or fragment thereof is cloned, the subsequent isolation and purification of other species cDNAs is substantially simplified.

EXAMPLE 2

Competition between monoclonals for specific antigen

Monoclonal antibodies which bind to distinct areas of an antigen molecule do not interfere with each other; on the other hand, monoclonal antibodies directed against the same or topographically related epitopes or antigenic determinants, will inhibit each other's activity. Thus, it is possible to map the epitopes of an antigen.

The number of epitopes of CS proteins which react with monoclonal antibodies was determined by an immunoradiometric assay performed as follows:

A) *Preparation of plates coated with sporozoite extracts.*

Sporozoites were purified from salivary glands of infected mosquitoes as described by Yoshida, N. et al, Science 207, 71 (1980). They were suspended in phosphate-buffered saline (PBS) at a concentration of $10^6$/ml and subjected to sonication (100 W for 3 minutes), then further diluted 20-fold in PBS. Then 50 ul of the suspension were delivered to the bottom of wells of Falcon "3911" microtiter plates, manufactured by Falcon Plastics, Oxnard, California. These were incubated overnight at 4°C and washed with PBS. The wells were then carefully washed with Tween-20 Trademark, Atlas Europol SpA, Ternate, Italy, (0.05% v/v) and incubated for 3 hours in PBS-containing 0.5% (w/v) bovine serum albumin (BSA) to saturate the hydrophobic sites of the plastic.

B) Preparation of monoclonal antibodies.

Monoclonal antibodies were raised against different species of sporozoites as described by Yoshida, et al, supra; and Potocnjak, P., et al, J. Exp. Med. 151, 1504 (1980). The antibodies were isolated from ascitic fluid of mice injected with the hybridomas by standard chromatographic procedures (ion exchange chromatography and filtration in Sephadex G-200). The purity of the antibodies was ascertained by SDS-PAGE. The antibodies were then radiolabeled with $^{125}I$ using Iodogen (Pierce Chemical Co., Rockford, Ill.) according to the instructions of the manufacturer. The specific activity varied between $10^7 - 3 \times 10^7$ cpm per $\mu g$ protein.

C) Titration of monoclonal antibodies.

The minimal concentration of a monoclonal antibody which saturates the antigen sites in the bottom of wells of microtiter plates was determined as follows:

To a series of tubes containing a constant amount (0.5 ng) of radiolabeled monoclonal antibody diluted in PBS-BSA, increasing amounts of cold antibody were added, maintaining a constant total volume. 30 $\mu l$ aliquots of the various mixtures containing the same number of counts, but different concentrations of antibody, were delivered to the bottom of individual wells of the microtiter plates pre-coated with specific antigen. After incubation for 1 hour at room temperature, the wells were washed with PBS-BSA and counted in a gamma counter. The greatest concentration of monoclonal antibody yielding a maximum of counts bound, represents the saturating dose of monoclonal antibody.

D) Competition between monoclonal antibodies for binding to the antigen

Several monoclonal antibodies were prepared against the CS proteins of P.knowlesi. The monoclonal antibodies were labeled with $^{125}I$ and the saturating dose determined as described, supra. Then, cross-titrations were performed as follows to determine whether each cold monoclonal antibody interfered with the binding of any other labeled monoclonal antibody to the solid-phase antigen.

To a series of antigen-containing wells, 50 μl of different concentrations of the various cold monoclonals diluted in PBS-BSA were added. The plates were incubated for 1 hour at room temperature. Then, 50μl of one of the radiolabeled monoclonals (for example, 2G3) at twice the saturating concentration, were added to all the wells. After an additional hour of incubation, the wells were washed and counted. The number of specific counts bound to antigen was calculated as the number of counts bound in wells incubated with 2G3 alone at the saturating dose minus the number of counts bound in wells incubated with 2G3 in the presence of cold 2G3 at a concentration $10^3$ times the saturating dose. The counts which could not be inhibited by the homologous cold antibody represent non-specific binding. From these numbers, the percentages of inhibition of binding of 2G3 by the other monoclonal antibodies were calculated. The titration was repeated for each labeled monoclonal antibody. The results are summarized in Table 1. It can be seen that all monoclonal antibodies to P.knowlesi strongly inhibit each other, indicating that they must bind to closely related or identical epitopes.

An identical procedure was followed to study the specificities of the monoclonal antibodies to P.vivax and P.falciparum (Tables II and III), P. malariae and P.berghei (not shown). The overall results demonstrate that there is a single immunodominant region in every CS protein.

EXAMPLE 3

Competition between monoclonal antibodies and polyclonal antisera for sporozoite antigens.

A) Assay for the binding of polyclonal antibodies to sporozoite extracts. The first step of this assay was essentially the same as that described in Example 2; that is, wells of microtiter plates were coated with crude sonicated extracts of sporozoites, washed with Tween-20 and saturated with PBS-BSA. Then, serial dilutions in PBS-BSA of the polyclonal antibodies to the homologous sporozoite species were prepared and aliquots of 30 μl delivered to the bottom of individual microtiter wells. Controls consisted of wells incubated with dilutions of polyclonal antibodies to an unrelated antigen. After an incubation of 4 hours at room temperature, the wells were washed. The presence of antibodies in the wells was detected with a second antibody ($^{125}$I-labeled and affinity-purified) to the immunoglobulin of the appropriate species. For example, in the case of human polyclonal antibodies, the second antibody consisted of 50 µl (µg/ml) of an affinity-purified rabbit anti-human Ig. The rabbit antibodies were polyspecific, reacting with human kappa, gamma and mu chains, and had been preabsorbed with mouse Ig. This absorption was necessary to prevent the interaction of the developing reagent with the mouse monoclonal antibodies used in the inhibition assay described below. When monkey polyclonal antibodies were used, the developing reagent was similarly prepared from a rabbit antiserum to monkey Ig.

B) Inhibition of binding of polyclonal antibodies by monoclonal antibodies

The wells coated with sporozoite extract were first incubated with a purified monoclonal antibody to the repetitive epitope of a CS protein, at saturating levels (see Example 2 for the determination of the saturating dose). After incubation for 1 hour at room temperature, the dilutions of the polyclonal antibodies were added, and the assay proceeded as described above.

Inhibition assays have been performed in the following systems:

1) P.knowlesi sporozoite extracts reacting with monkey antisera to X-irradiated P.knowlesi sporozoites. Inhibitory monoclonal antibody 2G3 (Cochrane, A. H., et al, Proc. Nat. Acad. Sci. USA 79, 565 (1982)).

2) P.vivax sporozoite extracts reacting with serum of humans vaccinated by the bite of X-irradiated P.vivax-infected mosquitoes. Inhibitory monoclonal antibody 2F2 (Nardin, E.H. et al, J. Exp. Med. 156:20 (1982)).

3) P.falciparum sporozoite extracts reacting with serum of humans vaccinated by the bite of X-irradiated P.falciparum-infected mosquitoes. Inhibitory monoclonal antibody 2A10 (Nardin, E.H., et al, supra).

Typical results of these assays are illustrated in

Figure 2. In every case, the monoclonal antibodies inhibited 70% or more of the interaction between the extracts and the polyclonal antibodies.

Considering that the solid-phase antigen is prepared by sonication of whole sporozoites and probably contains intracellular as well as plasma membrane proteins, these results indicate that a large proportion of the immune response in the polyclonal sera was directed against the repetitive epitope of the immunodominant region of the CS protein (see infra).

EXAMPLE 4

Presence of repetitive epitopes in the immunodominant region of CS proteins from several species of sporozoites.

The experiments in Examples 2 and 3 showed that the CS proteins of four species of Plasmodium contain a single immunodominant region. Shown in this section is the evidence that 1) all immunodominant regions contain a repetitive epitope, and 2) all monoclonals react with a repetitive epitope present in the immunodominant region.

The presence of repetitive epitopes in CS proteins is based on the observation that two-site immunoradiometric assays to measure CS proteins can be performed with a single monoclonal antibody. This is illustrated in Figure 3, for the CS proteins of P.vivax, P.falciparum, and P.knowlesi. Identical results were obtained with the CS protein of P.berghei and the monoclonal 3D11 (not shown) and the CS protein of P.malariae. The assays were performed as follows:

Wells of microtiter plates (Falcon 3911) were incubated overnight at 4°C with 50 μl of a 10 μg/ml solution in PBS of a monoclonal antibody. The wells were washed with PBS and incubated for 2 hours at room temperature with PBS-Tween 20 (0.05% v/v) and for 3 hours at room temperature with PBS-Tween 20-BSA (1% w/v). 30 ul of serial dilutions of extracts of sporozoites were delivered to the bottom of the wells, and the plates incubated overnight in the refrigerator. The extracts had been prepared by treating purified salivary gland sporozoites ($10^7$/ml) with 2% (v/v)NP-40 (Trademark, Particle Data Laboratories, Elmhurst, Ill.) in PBS for 2 hours at room temperature, followed by centrifugation at 100,000 g for 1 hour. The dilutions of the extract were made
in PBS-BSA containing 0.1% (v/v) NP-40. After incubation, the
wells were washed with PBS-Tween 20-BSA. Then 50 μl (about 5-10
ng) of the same $^{125}$I-labeled monoclonal antibody, diluted in
PBS-BSA-Tween 20, were added, and incubation at room temperature
proceeded for an additional hour. The wells were washed with
PBS-Tween 20-BSA and counted. Controls consisted of wells initially
coated with BSA alone. As shown in Figure 3, specific binding was
observed in every instance using the homologous antigen. These
experiments demonstrate that the various extracts of sporozoites
contain CS proteins which are at least divalent, since they can
bind two molecules of a single monoclonal antibody, one of them in
solidphase, attached to the plastic, and the other in fluid phase
and radiolabeled.

It could be argued, however, that the extracts contained
aggregated CS protein. This possibility was excluded by the
experiments described below, which show directly that the molecular
weight of the divalent or multivalent antigen in the extracts
corresponded to that of monomers of the CS proteins.

Extracts were prepared as described above treated with
SDS 2% (w/v) - 6M urea, and subjected to ultracentrifugation onto
5% (w/v) -20% (w/v) sucrose gradients. The runs were performed in
an ultracentrifuge, using a Beckman SW-20 50.1 (Trademark, Beckman
Instrument Co., Fullerton, California) rotor at 48,000 rpm for
20 hours. After centrifugation, the bottoms of the tubes were
perforated and drops collected in separate tubes. The fractions
were analyzed by two methods for the presence of CS protein.

1) Analysis of the fractions by the two-site immunoradio-
metric assay. This was performed with several monoclonal antibodies
for each extract, as described previously in this section. The
results of the assays are expressed as number of sporozoite
equivalents present in each fraction, as calculated from a standard
curve obtained on the same day of the experiment.

2) Analysis of the fractions by inhibition of binding of
monoclonals to antigen-coated plates. The gradient fractions were
also analyzed by an assay which detects single epitopes on the CS
protein. This assay was performed as follows: Antigen-coated plates were prepared, and the minimal saturating dose of radiolabeled monoclonal antibody was determined as described in Example 2. Aliquots of gradient fractions were mixed with the radiolabeled antibody for one hour at room rempterature, and then 30 μl of the mixtures were delivered to the wells containing solid-phase antigen. after an additional hour of incubation, the wells were washed and counted. The inhibition of binding is also expressed as number of sporozoite equivalents present in the fraction, as calculated from a standard curve.

The results of these experiments are summarized in Figs. 4 and 5, which also show the position in the fractions of marker proteins. The results show that the CS antigen of P.vivax and P.knowlesi was detected by both assays and sedimented in a single peak between the markers ovalbumin and bovine serum albumin. The amount of CS protein found in this peak represented 95% or more of the original input. Since CS proteins and their precursors have molecular weights between 40,000 and 60,000, these results strongly suggest that the extracts contain mainly or exclusively, monomers of these molecules. Moreover, all monoclonal antibodies tested recognized a repetitive epitope on the CS protein. The simplest explanation for this finding is that all of them react with the same epitope.

In short, the present results and those of the previous examples, demonstrate that the CS proteins of the human malaria parasites P.vivax, P.falciparum and P.malariae contain a single immunodominant region and repetitive epitopes, as in the case of P.knowlesi.

EXAMPLE 5

Cross-reactivity between species of sporozoites

The cross-reactions between the monoclonal antibodies to the repetitive epitopes of the CS proteins from various species of Plasmodium were detected by circumsporozoite (CSP) reactions or by the indirect immunofluorescence test. These tests are described in Nardin, E. H., et al, Nature 274, 55 (1978) and Danforth, H. D., et al, J. Parasitol, 64, 1123 (1978), and were performed with monoclonal antibodies.

For example, the CSP reaction is performed by incubation of dilutions of serum in PBS-BSA with purified viable salivary gland sporozoites at room temperature. After 10 minutes or more of incubation, the sporozoites are examined by phase-contrast microscopy. A positive reaction consists of a thread-like precipitate formed at the posterior end of the parasite. The CSP reaction does not occur in the cold, or with formaldehyde-fixed parasites. As demonstrated by Potocnjak, P., et al, supra, the CSP reaction is caused by the cross-linking of the CS protein by antibodies.

The indirect immunofluorescence test is performed with glutaraldehyde-fixed sporozoites. The parasites are treated with 1% (v/v) glutaraldehyde solution in PBS for 30 minutes at 0°C. Then they are washed in PBS, and incubated overnight with 0.1% (w/v) glycine in water. After washing by centrifugation, the resuspended sporozoites are deposited within 10 $\mu$l droplets on microscopic slides, at a concentration of 2 X $10^6$/ml. The droplets are air-dried and kept at -70°C. The assay is performed by incubation of the sporozoites with dilutions of the immune serum for 2 hours at room temperature, followed by washings with PBS, and a new incubation for 2 hours with a second antibody, fluorescein-labeled, directed against the Ig of the first immune serum. The second antibody (for example, rabbitanti-human Ig) can be obtained from a commercial source (Cappel Laboratories, Cochranville, Pa.). After washing, the slides are viewed with a fluorescence-microscope.

Using both procedures, the following cross-reactions were observed between monoclonal antibodies to the repetitive epitopes of the CS protein:

A) anti-P.knowlesi reacted with P.falciparum and P.cynomolgi;

B) anti-P.cynomolgi reacted with P.vivax;

C) anti-P.yoeli nigeriensis reacted with P.berghei. In this case the cross-reactive monoclonal antibodies even neutralized the infectivity of the heterologous species; and D) anti-P.malariae reacted with P.brasilianum.

EXAMPLE 6

Reactivity of synthetic peptides with monoclonal antibodies to the repetitive epitope of P.knowlesi The two synthetic peptides described in Example 1 were used in these studies. One of them was composed of the 12 amino acid sequence. $H_2N$-GlnAlaGlnGlyAspGlyAlaAsnAlaGlyGlnPro-COOH (12-MER) and the other was a dimer of the same sequence (24-MER). The 24-MER (but not the 12-MER) was directly shown by immunoradiometric assay to contain two epitopes of the CS protein of P.knowlesi. The assay was performed as follows:

Wells of microtiter plates (Falcon 3911) were incubated overnight at 4°C with 50 μl of a 10 μg/ml solution in PBS of the monoclonal 2G3 anti-CS protein of P.knowlesi. The wells were washed with PBS and then incubated for 2 hours at room temperature, with PBS-Tween 20 (0.05% (w/v), and then for 3 additional hours with PBS-BSA (1% (w/v). The synthetic peptides were diluted serially in PBS-BSA-Tween 20, and 30 ul aliquots of the dilutions were delivered to the bottom of individual wells. The plates were incubated overnight in the refrigerator, washed with PBS-BSA-Tween 20, and incubated with 5.0 ul (10 ng) of $^{125}$I-labeled monoclonal antibody 2G3 diluted in PBS-BSA-Tween 20 (about 100,000 cpm). Controls consisted of plates coated with a non-relevant monoclonal antibody of the same isotype as 2G3. The results are shown in Table IV. Specific counts were found only in wells incubated with the 24-MER and they were proportional to the dose of peptide added to the well.

No specific counts of the 24-MER were bound to the wells in which the solid-phase antibody was the monoclonal 3D11, which is directed against the CS protein of P.berghei.

These results strongly suggest that the 24-MER contains two identical epitopes recognized by the monoclonal 2G3, and that the 12-MER contains either one epitope or none. To distinguish between these possibilities, an assay was conducted to determine the ability of the 12-MER to inhibit the interaction between the CS proteins of P.knowlesi and the monoclonal antibody 2G3. The inhibition assay was performed as follows:

Wells of microtiter plates were coated with the monoclonal antibody 2G3 washed with Tween-20, saturated with BSA as described supra. In one series of tubes, the 12-MER was serially diluted in PBS-BSA-Tween 20. In a second series of tubes, an extract of P.knowlesi sporozoites (prepared as described by Cochrane, et al, supra) was serially diluted in PBS-BSA-Tween 20. Aliquots of each dilution of sporozoites were mixed with equal volumes of all dilutions of 12-MER. 30 μl of these mixtures were then added to the bottom of the 2G3-coated wells. As positive and negative controls, 30 μl aliquots of sporozoite dilutions mixed with PBS-BSA-Tween 20 were added to other wells which had been pre-coated with 2G3 or with a non-relevant monoclonal antibody. After overnight incubation in the refrigerator, the wells were washed and 50 μl (10 μg) of $^{125}$I-labeled 2G3 diluted in PBS-BSA-Tween 20 were added. Following an additional incubation at room temperature for 1 hour, the wells were washed and counted in a gamma counter. The results are shown in Table V. The 12-MER inhibited, in a dose-dependent fashion, the interaction of the P.knowlesi CS protein with 2G3.

The conclusion drawn from this experiment is that the 12-MER peptide contains an epitope of the CS protein of P.knowlesi.

The reactivity of the synthetic peptides was confirmed by radiolabeling the 24-MER and showing that it bound specifically a monoclonal antibody to P.knowlesi (5H8). This experiment was performed as follows:

A) Preparation of Sepharose-4B (Trademark, Pharmacia, Inc. Uppsala, Sweden) coupled to the monoclonal antibodies 5H8 and 3D11, directed against the CS proteins of P.knowlesi and P.berghei respectively.

The antibodies were coupled to CNBr Sepharose beads (Pharmacia Fine Chemicals Uppsala, Sweden) following the instructions of the manufacturer. After coupling, the beads (containing about 10 mg antibody/ml) were treated for 1 hour at room temperature with 0.5% glutaraldehyde (to prevent leakage of the proteins), then with a solution of 10 mg/ml glycine in PBS, and finally resuspended at 20% volume in PBS-BSA (1% (w/v)) Tween 20 (0.05% (v/v)). The Sepharose-coupled monoclonals were designated Sepharose-5H8 and Sepharose 3D11, respectively.

B) Radiolabeling of the 24-MER was performed with $^{125}$I using the Bolton-Hunter reagent (Amersham International Ltd., Amersham, U.K.) according to the instructions of the manufacturer, using 10 μl of a solution of the 24-MER (10 mg/ml) and 0.1 millicuries of the Bolton-Hunter reagent. The peptide was purified after labeling in a Sephadex-G10 column equilibrated in PBS-gelatin (0.2% (w/v)). Presuming that 100% of the peptide was recovered, the specific activity was $10^5$-cpm/μg of protein.

C) Specific binding of the radiolabeled 24-MER to Sepharose-5H8.

Four 200 μl aliquots of the 20% (w/v) suspension of Sepharose-5H8 were added to tubes containing 150 μl of a dilution of the labeled 24-MER in PBS-BSA-Tween 20 (45,000 cpm). To two of the tubes 50 ul of diluent were added. To the other two tubes 50 ul of cold 24-MER (500 μg) diluted in PBS-BSA-Tween 20 were added. The tubes were incubated overnight in the refrigerator. The beads were washed by centrifugation and counted.

As controls, identical mixtures were prepared in tubes containing Sepharose-3D11. The results are shown in Table VI. These results demonstrate that the radiolabeled peptide bound specifically to the monoclonal antibody 5H8 anti-CS protein of P.knowlesi. In addition, it appears that the 24-MER may have interacted weakly with the 3D11 antibody. This is not surprising, considering the evidence that all CS proteins are structurally related, and that, in these experiments, the molar ratio of antibody to the ligand peptide was quite high.

EXAMPLE 7

Immunization with the synthetic repeated epitope of P.knowlesi (24-MER)

The synthetic 24-MER is synthesized as described in Example 1, except that a cysteine residue is added at the N-terminus. To determine whether the synthesis has been performed correctly, an aliquot is subjected to acid hydrolysis at reduced pressure (6M HCl, 110°C, 72 hours) and its amino acid composition is determined. The peptide is coupled to a carrier protein either keyhole limpet hemocyanin, or tetanus toxoid, through its N terminal cysteine residue, using m-maleimidolbenzoyl-N-hydroxysuccinimide ester (MBS) as the coupling reagent (Ling, F. T., et al, Biochemistry 18, 690 (1979)). This is a bi-functional reagent which under appropriate conditions reacts specifically with the amino group of the carrier on the one hand, and with the thiol group of the peptides, on the other hand.

4 mg of the carrier protein in 0.25 ml of 0.05M $PO_4$ buffer, pH 7.2, is reacted dropwise with 0.7 mg MBS dissolved in dimethyl-formamide, and stirred for 30 min. at room temperature. The product, that is, MB-carrier, is separated from the unreacted chemicals by passage in a Sephadex G-25 column equilibrated in 0.05M $PO_4$ buffer, pH 6.0. The MB-carrier is then reacted with 5 mg of the 24-MER containing cysteine, dissolved in PBS (pH 7.4). The mixture is stirred for 3 hours at room temperature. Coupling efficiency is monitored with radioactive peptide; that is, a trace amount of $^{125}I$-labeled 24-MER is mixed with cold peptide during the synthesis. Dialysis of the conjugate permits evaluation of the proportion of incorporated label. The number of 24-MER groups per 100,000 M.W. carrier was estimated to be about 10-14.

Five rhesus monkeys are immunized with 200 mg of the conjugated protein adsorbed to aluminum hydroxide gel. Their serum is monitored for the presence of antibodies to CS proteins of P.knowlesi by the immunoradiometric assay described in Example 3. That is, serum dilutions are incubated with antigen-coated wells of microtiter plates. The presence of monkey antibody bound to the solid-phase antigen is monitored by incubation with $^{125}I$-labeled affinity-purified rabbit-anti-human Ig (which strongly cross-reacts with rhesus monkey Ig).

After 30 days, the serum titers of the monkeys rise to titers of greater than 1/1000. At this time, these monkeys (as well as five other control monkeys injected with non-conjugated carrier protein adsorbed to aluminum hydroxide) are challenged with 2,000 viable P.knowlesi sporozoites. The infection is monitored daily for a total of 30 days by microscopic examination of blood smears, starting one week after the inoculation of the parasites. The results show that the five monkeys immunized with the vaccine (conjugated protein) are totally protected; that is, no parasites are found in their blood. In contrast, the control monkeys have trophozoites of P.knowlesi in the circulation 7-12 days after challenge.

EXAMPLE 8

Immunization with the synthetic repeated epitopes of P.vivax and P.falciparum The synthetic sequences corresponding to the repeated epitopes of P.vivax and P.falciparum are synthesized essentially as described in Example 1, except that cysteine residues are added at the N-terminals as described in Example 7. To determine whether the synthesis has been performed correctly, aliquots are subjected to acid hydrolysis at reduced pressure (6M HCl, 110°C, 72 hours) and their amino acid composition is determined.
The peptides are coupled to a carrier protein either keyhole limpet hemocyanin, or tetanus toxoid, through its N terminal cysteine residue, by using MBS as the coupling reagent, as described in Example 7.

4 mg of the carrier protein in 0.25 ml of 0.05M $PO_4$ buffer, pH 7.2., is reacted dropwise with 0.7 mg MBS dissolved in dimethyl-formamide, and stirred for 30 min. at room temperature. The product, that is, MB-carrier, is separated from the unreacted chemicals by passage in a Sephadex G-25 column equilibrated in 0.05M $PO_4$ buffer, pH 6.0. The MB-carrier is then reacted with 5 mg of each peptide containing cysteine, dissolved in PBS (pH 7.4). The mixture is stirred for 3 hours at room temperature. Coupling efficiency is monitored with radioactive peptide; that is, a trace amount of $^{125}I$-labelled is mixed with cold peptide during the synthesis. Dialysis of the conjugate permits evaluation of the proportion of incorporated label. The number of synthetic peptides per 100,000 M.W. carrier is estimated to be about 10-14.

Five chimpanzees are immunized with 200 µg of each of the conjugated proteins adsorbed to aluminum hydroxide gel. Their serum is monitored for the presence of antibodies to CS proteins of P.vivax and P.falciparum by the immunoradiometric assay described in Example 3. That is, serum dilutions are incubated with antigen-coated wells of microtiter plates. The presence of chimpanzee antibody bound to the solid-phase antigen is monitored by incubation with $^{125}I$-labeled affinity-purified rabbit-anti-human Ig (which strongly cross-reacts with chimpanzee Ig).

After 30 days, the serum titers of the chimpanzees rise to titers of greater than 1/1000. At this time, these chimpanzees (as well as five other control chimpanzees injected with non-conjugated carrier protein adsorbed to aluminum hydroxide) are challenged with 2,000 viable P.vivax sporozoites. The infection is monitored daily for a total of 30 days by microscopic examination of blood smears, starting one week after the inoculation of the parasites. The results show that the five chimpanzees immunized with the vaccine (conjugated protein) are totally protected; that is, no parasites are found in their blood. In contrast, the control chimpanzees have trophozoites of P.vivax in the circulation 10-12 days after challenge.

Next, a second challenge with 10,000 P.falciparum sporozoites is given to the same chimpanzees. Again the vaccinated apes are protected, while the controls are all infected.

Based upon the close similarities of human and chimpanzee immune responses and on the fact that protective immunity has been obtained in humans by injection of inactivated sporozoites of P.falciparum and for P.vivax, the results obtained upon immunization of chimpanzees with the described synthetic peptide will also be obtained following similar treatment of human patients.

FIG. 1

Galactosidase Fusion protein Containing Plasmodium Knowlesi CS Protein Immunogenic Region

```
         10        20        30        40        50        60        70        80        90
ATGAGTATTCAACATTTCCGTGTCGCCCTTATTCCCTTTTTTGCGGCATTTTGCCTTCCTGTTTTTGCTCACCCAGAAACGCTGGTGAAAGTAAAAGATG   100
MetSerIleGlnHisPheArgValAlaLeuIleProPhePheAlaAlaPheCysLeuProValPheAlaHisProGluThrLeuValLysValLysAspA

CTGAAGATCAGTTGGGTGCACGAGTGGGTTACATCGAACTGGATCTCAACAGCGGTAAGATCCTTGAGAGTTTTCGCCCCGAAGAACGTTTTCCAATGAT   200
laGluAspGlnLeuGlyAlaArgValGlyTyrIleGluLeuAspLeuAsnSerGlyLysIleLeuGluSerPheArgProGluGluArgPheProMetMe

GAGCACTTTTAAAGTTCTGCTATGTGGCGCGGTATTATCCCGTGTTGACGCCGGGCAAGAGCAACTCGGTCGCCGCATACACTATTCTCAGAATGACTTG   300
tSerThrPheLysValLeuLeuCysGlyAlaValLeuSerArgValAspAlaGlyGlnGluGlnLeuGlyArgArgIleHisTyrSerGlnAsnAspLeu

GTTGAGTACTCACCAGTCACAGAAAAGCATCTTACGGATGGCATGACAGTAAGAGAATTATGCAGTGCTGCCATAACCATGAGTGATAACACTGCGGCCA   400
ValGluTyrSerProValThrGluLysHisLeuThrAspGlyMetThrValArgGluLeuCysSerAlaAlaIleThrMetSerAspAsnThrAlaAlaA

ACTTACTTCTGACAACGATCGGAGGACCGAAGGAGCTAACCGCTTTTTTGCACAACATGGGGGATCATGTAACTCGCCTTGATCGTTGGGAACCGGAGCT   500
snLeuLeuLeuThrThrIleGlyGlyProLysGluLeuThrAlaPheLeuHisAsnMetGlyAspHisValThrArgLeuAspArgTrpGluProGluLe

GAATGAAGCCATACCAAACGACGAGCGTGACACCACGATGCCTGCAGGGGGGGGGGGGGGGGGGGGGGTGATGGAGCAAATGCAGGACAACCACAAGCA   600
uAsnGluAlaIleProAsnAspGluArgAspThrThrMetProAlaGlyGlyGlyGlyGlyGlyGlyGlyAspGlyAlaAsnAlaGlyGlnProGlnAla

CAAGGAGATGGAGCAAATGCAGGACAACCACAAGCACAGGGTGATGGAGCAAATGCAGGACAACCACAAGCACAGGGTGATGGAGCAAATGCAGGACAAC   700
GlnGlyAspGlyAlaAsnAlaGlyGlnProGlnAlaGlnGlyAspGlyAlaAsnAlaGlyGlnProGlnAlaGlnGlyAspGlyAlaAsnAlaGlyGlnP

CACAAGCACAAGGAGATGGAGCAAATGCAGGACAACCACAAGCACAGGGTGATGGAGCAAATGCAGGACAACCACAAGCACAGGGTGATGGAGCAAATGC   800
roGlnAlaGlnGlyAspGlyAlaAsnAlaGlyGlnProGlnAlaGlnGlyAspGlyAlaAsnAlaGlyGlnProGlnAlaGlnGlyAspGlyAlaAsnAl

AGGACAACCACAAGCACAAGGAGATGGAGCAAATGCAGGACAACCACAAGCACAAGGAGATGGAGCAAATGCAGGACCCCCCCCCCCCCCCCCTGCAGCA   900
aGlyGlnProGlnAlaGlnGlyAspGlyAlaAsnAlaGlyGlnProGlnAlaGlnGlyAspGlyAlaAsnAlaGlyProProProProProProAlaAla

ATGGCAACAACGTTGCGCAAACTATTAACTGGCGAACTACTTACTCTAGCTTCCCGGCAACAATTAATAGACTGGATGGAGGCGGATAAAGTTGCAGGAC   1000
MetAlaThrThrLeuArgLysLeuLeuThrGlyGluLeuLeuThrLeuAlaSerArgGlnGlnLeuIleAspTrpMetGluAlaAspLysValAlaGlyP
```

```
CACTTCTGCGCTCGGCCCTTCCGGCTGGCTGGTTTATTGCTGATAAATCTGGAGCCGGTGAGCGTGGGTCTCGCGGTATCATTGCAGCACTGGGGCCAGA  1110
roLeuLeuArgSerAlaLeuProAlaGlyTrpPheIleAlaAspLysSerGlyAlaGlyGluArgGlySerArgGlyIleIleAlaAlaLeuGlyProAs

TGGTAAGCCCTCCCGTATCGTAGTTATCTACACGACGGGGAGTCAGGCAACTATGGATGAACGAAATAGACAGATCGCTGAGATAGGTGCCTCACTGATT  1200
pGlyLysProSerArgIleValValIleTyrThrThrGlySerGlnAlaThrMetAspGluArgAsnArgGlnIleAlaGluIleGlyAlaSerLeuIle

AAGCATTGGTAA
LysHisTrp***
```

-- Appendix B

Text of Related Application Serial No. 77,006 Incorporated by Reference

PROTECTIVE PEPTIDE ANTIGEN CORRESPONDING TO PLASMODIUM FALCIPARUM CIRCUMSPOROZOITE PROTEIN

Background of the Invention

The present invention relates to an antigen suitable for providing protective immunity against malaria e.g. by incorporation into a vaccine. A formidable health problem in large areas of the world, malaria affects more than 150 million people in any given year. Of the four plasmodial species which cause malaria in humans, Plasmodium falciparum is responsible for most of the severe infections and the highest rate of mortality. Combating malarial infestations caused by P.falciparum has become more difficult due to the spread of drug-resistant organisms in many areas. The occurrence of severe epidemic outbreaks of this disease lends particular urgency to recent efforts to develop a malaria vaccine.

Under normal conditions, a malarial infection is initiated by the introduction of sporozoites into the bloodstream of the host through the bite of infected mosquitoes. Hence, inactivation of these sporozoites by the immune system of the host could completely block development of the infection. Several recent findings point to the feasibility of developing an antisporozoite vaccine. Sporozoites are highly immunogenic and are capable of eliciting a protective immune response in several host species, including man: see e.g. Cochrane, A.H. et al. Malaria, Vol. 3, J.D. Kreier, Ed. (Academic Press, New York 1980), pp. 163-202. The immunogenicity of sporozoites resides largely, if not exclusively, in a single antigen, the circumsporozoite (CS) protein (described in detail by F. Zavala, A.H. Cochrane, E.H. Nardin, R.S. Nussenzweig, V. Nussenzweig, J. Exp. Med. 157: 1947 (1983), which covers the entire parasite surface, as reported by M. Aikawa, N. Yoshida, R.S. Nussenzweig and V. Nussenzweig in Journal of Immunology, 126: 2494 (1981). Finally, the immunogenicity of the CS protein is restricted almost entirely to a single epitope which is identically or quasi-identically repeated several times in tandem: G.N. Godson, et al. Nature 305: 29 (1983); V. Enea et al., accepted for publication Proc. Nat'l. Acad. Sci. (1984).

Identification of the amino acid sequence of CS epitopes for all plasmodial species that infect humans is a prerequisite for the development of a human synthetic sporozoite vaccine.

Several monoclonal antibodies have been raised against the CS protein of Plasmodium falciparum sporozoites. These antibodies inactivate the parasites. Methods for obtaining such antibodies are well known in the art and have been disclosed by Nardin E. et al. in J. Exp. Med. 156: 20 (1982), and in U.S. Patent Application Serial No. 234,096 of Nussenzweig et al, filed February 12, 1981 the disclosure of which is incorporated herein by reference. (The disclosure of this application also incorporates by reference the entire disclosure of assignee's copending U.S. Patent Application Serial No. 574,553 filed January 27, 1984 of Nussenzweig, et al. entitled Protective Peptide Antigen).

These monoclonal antibodies against CS protein bind to a repeated epitope, which is common to different isolates of parasites obtained from different geographical areas. Such antibodies can be used to screen clones expressing peptides having or incorporating the amino acid sequence of the CS repetitive epitopes.

Antibodies against the sporozoite antigens have been shown to provide protective immmunity against the plasmodium species from which they were derived, in rodents, monkeys and in human volunteers. The sporozoite protective antigen is herein termed CS protein, or circumsporozoite protein, or sporozoite CS protein, these terms being deemed equivalent and used interchangeably. Assignee's copending U.S. Patent Application of Nussenzweig, Serial No. 234,096 filed February 12, 1981 discloses a vaccine based upon purified CS protein. Assignee's copending application Serial No. 574,553 discloses a peptide comprising an epitope of a sporozoite CS protein.

The results disclosed herein are based in part on techniques and concepts in the field of immunology. For convenience, certain terms commonly used in the art are defined herein. The term "immunochemical reaction" is used to denote the specific interaction which occurs between an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art. The terms "immunogenic" or "antigenic" are used here to describe the capacity of a given substance to stimulate the production of antibodies specifically immunoreactive to a substance when that substance is administered to a suitable test animal under conditions known to elicit antibody production. The term "protective antigen" refers to the ability of a given immunogen to confer resistance in a suitable host, against a given pathogen. The term "epitope", refers to a specific antibody binding site on an antigen. Macromolecular antigens such as proteins typically have several epitopes with distinctive antibody binding specificities. Different epitopes of the same antigen are distinguishable with the aid of monoclonal antibodies which, due to their high degree of specificity, are directed against a single epitope. Two different monoclonal antibodies directed against different epitopes on the same antigen may bind the antigen without interfering with the other, unless the epitopes are so close together that the binding of one sterically inhibits the binding of the other. The term "immunodominant region" denotes an area of the antigen molecule which is mainly responsible for its antigenicity.

Summary of the Invention

The present invention involves the discovery that the protective CS sporozoite antigens of P. falciparum possess an immunodominant region composed of four amino acids (proline-asparagine-alanine-asparagine) that are tandemly repeated at least 23 times. The repeat comprises 8 variants at the nucleotide level. Both asparagine codons, three of the four proline codons and two of the four alanine codons are employed. This repeated sequence has been shown to contain the epitope of the CS protein of Plasmodium falciparum. Analogs of the repeated peptide have been chemically synthesized and have been found to be immunochemically reactive with polyclonal antibody preparations against Plasmodium falciparum. In addition, monoclonal antibodies against CS proteins, which neutralize the infectivity of sporozoites in vitro, also react with the synthetic peptide. Vaccines made with three and six tandem repeats of the four amino acid sequence (12-MER and 24-MER peptides) confer immunity to P. falciparum sporozoites. Thus, these synthetic peptides exhibit the protective antigenic features of the P. falciparum CS protein.

Detailed Description of the Invention

In the following description, the materials employed were commercially available, unless otherwise specified. Enzymes used in the cloning procedures were obtained from commercial sources. Restriction endonuclease reactions were carried out according to the manufacturer's instructions. Unless otherwise specified, the reaction conditions for other enzyme reactions were standard conditions used in the art, as described, for example, in Methods in Enzymology, (Vol. 68, R.Wu, Ed.) Academic Press, (1980). Unless otherwise specified, the abbreviations herein are standard abbreviations acceptable for publication in scientific journals normally used by those skilled in the art to publish their results, such as those cited herein.

Monoclonal antibodies to P.falciparum sporozoites were isolated from mouse ascites injected with hybridomas produced by fusing the spleen cells of P.falciparum sporozoite-hyperimmunized mice with NS1 myeloma cells as described in Nardin, E.H., et al J. Exp. Med. 156:20-30 (1982). The monoclonal antibody used to identify the clone expressing the protective peptide antigen of the present invention was prepared according to the procedures of Nardin, et al., supra, and designated "2A10."

In general outline, the experiments and conclusions following from the results thereof are set forth. The synthetic protein of the present invention was defined and initially secured by cloning a cDNA made from mRNA obtained from infected mosquitoes. A cDNA library was constructed from poly (A)$^+$ RNA derived from Plasmodium falciparum infected mosquitoes. Double-stranded cDNA was inserted at the PstI site of plasmid pBR322 using the dC-dG tailing method to generate recombinant plasmids that could express the inserts as a fusion protein with the beta-lactamase encoded by the vector. Bacterial host cells (LE 392 derived from E. coli K-12) were transformed and the resulting tetracycline resistant DNA molecules were screened for the expression of CS antigen using an in situ filter immunoassay.

Approximately 10,000 colonies were screened by an in situ radioimmunoassay with the monoclonal antisporozoite antibody (2A10) and a strongly positive clone, designated p277-19 was identified.

Extracts of the host bacterium LE392, harboring the plasmid p277-19 were then tested in a two-site immunoradiometric assay by using monoclonal antibody 2A10 immobilized in plastic wells, and the same [$^{125}$I]-labelled antibody in the fluid phase: F. Zavala et al, Nature 229: 737 (1982).

The recombinant protein expressed by clone p277-19 is able to bind simultaneously both the immobilized and the radiolabelled antibody. This indicates that the recombinant protein, as the authentic CS protein, contains at least two epitopes which are recognized by the anti-CS monoclonal antibody 2A10.

The nucleotide sequence of the p277-19 insert is illustrated in Fig. 1. In the protein encoded by this sequence, the amino acid sequence proline, asparagine, alanine and asparagine is repeated 23 times in tandem with no variations. This repetitive pattern of four amino acids is the shortest of the known CS protein repeats. The repeats of P. knowlesi and P. cynomolgi (Gombak strain), two simian malaria parasites, are twelve and eleven amino acids long, respectively, Godson, et al. Nature 305: 29 (1983); V. Enea et al. supra (1984).

Although neither the DNA nor the protein sequences of these repeated peptides are related to one another, certain similarities are apparent from an analysis of their amino acid composition. Thus, alanine and asparagine are present in the repeats of all known CS proteins; proline is present in P. knowlesi and P. falciparum; and glutamic acid and glycine are present in P. knowlesi and P. cynomolgi (gombak).

The present findings indicate that the immunodominant epitope of the CS protein of P. falciparum consists of a sequence of amino acids which does not appear to require further modification to be antigenic.

EXAMPLE I.

Preparation of Plasmodium falciparum RNA

RNA was prepared from the thoraces of Anopheles balabacensis mosquitoes infected with Plasmodium falciparum of the Thai K-1 stain. The collected thoracic tissue (from 1837 mosquitoes) was homogenized in 10 volumes of 4 M guanidine isothiocyanate (pH 5.0) and 0.1M 2-mercaptoethanol (Liu et al, Proc. Nat'l Acad. Sci. (USA) 76:4503 1979; Ellis et al, Nature 302:536 (1983). The homogenate was centrifuged at 9,000 rpm for three minutes in a Sorval (RC2-6) centrifuge. The supernatant was then layered over 0.2 volumes of 5.7M cesium chloride and 0.1 EDTA (pH 6.5) and centrifuged in an SW-41 rotor at 28K for 16 to 20 hours at 20°C. The RNA pellet was resuspended in 7.5M guanidine hydrochloride in 25 mM sodium citrate (pH 7.0) with 5 mM beta-mercaptoethanol. The RNA was precipitated by adding one fortieth volume, 1 M acetic acid and one half volume of 95% ethanol at -20°C for two to three hours (Chirgwin, et al. Biochem. 18:5294 1979). This was followed by a second precipitation in 0.3M sodium acetate (pH5) and 2.5 volumes of 95% ethanol, overnight at -20°C. Following centrifugation the RNA pellet was resuspended in water and stored at -70°C.

EXAMPLE II.

Purification of the Poly(A)$^+$ RNA

Poly (A)$^+$ RNA was prepared according to the method of Aviv and Leder Proc. Nat'l Acad. Sci. (USA) 69:1408 (1972). The RNA was heated at 68°C for 10 minutes, then chilled on ice for 5 minutes. After warming the RNA sample to room temperature, binding buffer was added to a final concentration of 0.5M sodium chloride, 0.01M Tris-HCl (pH 7.4) and 0.01M EDTA (pH 7.0). The RNA was cycled 3-5 times through an oligo(dT) cellulose (Collaborative Research, Inc., Waltham, Mass.) column with a bed volume of 0.2 - 0.4 ml. The poly(A$^+$) RNA was eluted from the column with sterile water at room temperature. The RNA was recovered by precipitation with ethanol, and stored in water at -70°C.

Prior to the cDNA synthesis, 1.5 micrograms of the poly(A)$^+$ RNA was mixed with 75 nanograms of rabbit globin mRNA (Bethesda Research Laboratories, (BRL), Bethesda, Md.) extracted first with phenol and chloroform (1:1 v/v) and then with chloroform. The RNA was precipitated in 0.3 M sodium acetate and 2 and $^1/2$ volumes of 95% ethanol. The pellet was resuspended in six microliters of water and then stored at $-70°C$.

EXAMPLE III.

Construction of the cDNA Library from Poly (A)+ RNA

The first and second strands of the cDNA were synthesized by a modification of the procedure of Okayama and Berg, Molecular and Cellular Biology 2:161 (1982). Approximately 1.5 micrograms of P. falciparum poly(A)$^+$ RNA mixed with 75 nanograms of rabbit globin mRNA (Bethesda Research Laboratories), were incubated in a 30 microliter reaction volume containing 50 mm Tris-HCl (pH 8.3), 50 mm KCl, 8 mm $MgCl_2$, 2 mm dithiothreitol, 30 micrograms/ml oligo-$dT_{(12-18)}$ cellulose (Collaborative Research), 100 micrograms/ml Actinomycin-D (Sigma Chemical Co., St. Louis, Mo.), 100 micrograms/ml BSA (bovine serum albumin), 0.25 mM dATP, 0.5 mM dCTP, 0.5 mM dGTP, 0.5 mM dTTP, $50 \times 10^{-6}$ Ci alpha-[$^{32}$P] dATP (specific activity 3,000 curies per millimole) and 120 units of reverse transcriptase (BRL) at $42°C$ for 2 hours.

The reaction was stopped by extraction with phenol and chloroform (1:1 v/v), then with an equal volume of chloroform and precipitated two times with 2 M ammonium acetate and ethanol. The pellet was washed with 80% ethanol, dried by dessication under vacuum, and resuspended in 46.9 microliters of water.

The second strand was synthesized in a 65 microliter reaction volume containing 20 mM of Tris-HCl (pH 7.4), 4 mM of magnesium chloride, 10 mM $(NH_4)_2SO_4$, 0.1 mM of KCl, 50 micrograms/ml BSA, 0.3 mM nicotinamide adenine dinucleotide (NAD) oxidized (Sigma), 0.1 mM each of the deoxynucleotide triphosphates (dATP, dCTP, dTTP, dGTP[1/]), one unit DNA Polymerase I (Boerhinger Mannheim Biochemical, Indianapolis, Indiana), 1.5 units RNAase H (BRL), 1 unit E.Coli ligase (P.L. Biochemical). The reactants were first incubated at $15°C$ for one hour, then

---

[1/] This and all dNTP's were from P.L. Biochem., Milwaukee, Wisc.

at room temperature for one hour. Again, the reaction was stopped by extraction, first with phenol/ chloroform (1:1) and then with an equal volume of chloroform. The mixture was precipitated once with 2M ammonium acetate and ethanol and the pellet washed with 80% ethanol, dried and resuspended in 4.5 microliters of water.

The second strand synthesis reaction was completed with $T_4$ DNA polymerase (BRL). The double stranded cDNA was incubated in 50 mM Tris-HCl (pH 8.0), 6 mM magnesium chloride, 25 mM KCl, 0.1 mM each of dATP, dCTP, dGTP and dTTP and 3.5 units of $T_4$ DNA Polymerase at 37°C for 30 minutes. The reaction was stopped by the addition of 25 mM EDTA. The reaction mixture was extracted with phenol and chloroform (1:1 v/v), and then with an equal volume of chloroform, followed by three washes with ether. The double-stranded cDNA was then precipitated with 0.5 M NaCl and 10% PEG (polyethylene glycol, average molecular weight 8,000) at 4°C overnight. The double-stranded cDNA was tailed with deoxycytidine residues according to Roychoudhury, et al. Nucl. Acids Res., 3, 101 (1976); Land et al. Nucl. Acids Res. 9:2251 (1981). Double-stranded cDNA (30 to 60 nanograms) were incubated in a 25 microliter reaction volume with 0.1 M potassium cacodylate (pH 7.0), 0.5 mM dCTP, 0.1 mM DTT and 2 mM $CoCl_2$ at 37°C for five minutes. Ten units of terminal deoxynucleotidyl transferase (Enzo Biochemical, Inc.) were added and the mixture was incubated at room temperature for 1 minute. The reaction was stopped by the addition of EDTA to 10 mM. Two micrograms of yeast tRNA were added and the mixture was extracted twice with phenol/chloroform (1:1) and once with chloroform, and then precipitated with 2M ammonium acetate and ethanol.

The deoxy(C)-tailed double-stranded cDNA was resuspended in 60 microliters annealing buffer (10 mM Tris-HCl, pH 7.4, 100 mM NaCl, and 1 mM EDTA). The concentration was estimated to be 0.6 to 3 micrograms/ microliter. The tailed cDNA was annealed (using the method of Land, et al. supra 1981) to PstI-cut and deoxy(G)-tailed pBR 322 (New England Nuclear) at varying ratios to determine the optimal ratio of insert to vector.

All of the pilot annealings were performed at a concentration of 250 nanograms pBR322/ml in a 200 microliter reaction volume by mixing 50 ng of pBR322 with 20, 8.0, 4.2 and 3.3 microliters of the tailed double-stranded cDNA. The 20 and 4.2 microliter pilot reactions yielded the maximum number of colonies and therefore were scaled up to make larger preparations for transformation.

EXAMPLE IV

Transformation of Host Cells

E. coli LE 392 cells were used as the bacterial host (P. Leder, et al. Science 196:175 (1977)). This is a variant of the E. coli K-12 strain. However, transformation may also be carried out in other host cells such as, DH1 available from the E. Coli Genetic Stock Center, Yale Univ. (CGSC No. 6040).

The host cells were transformed by the recombinant plasmids using a modification of the procedure of Banahan et al. J. Mol. Biol., 166: 557-580 (1983). 2.5 nanograms of the hybrid plasmid were added to 210 microliters of competent LE 392 cells. The mixture was incubated on ice for 30 minutes, heat shocked at 42°C for 90 seconds and placed on ice for 1 to 2 minutes. 800 microliters of SOC (2% Bactotryptone (Difco Detroit, Mich.), 0.5 % yeast extract, 10 mM NaCl, 2.5 mM KCl, 10 mM $MgCl_2$, 10 mM $MgSO_4$, 20 mM glucose) were added and the reaction was incubated at 37°C shaking at 225 rpm for one hour. The cells were centrifuged at 2,000 rpm for 10 minutes and resuspended in 0.4 milliliters SOB without magnesium (2% Bactotryptone, 0.5% yeast extract, 10 mM NaCl, 2.5 mM KCl) and spread on two Banahan plates (1% Bactotryptone, 0.95% yeast extract, 10 mM NaCl, 1.5% Bacto agar) with 12.5 micrograms/ml of tetracycline (Sigma). The transformation efficiency was approximately $10^5$ transformants per microgram of annealed DNA.

EXAMPLE V

Screening for the cDNA Library

The cDNA library was screened by a modification of the in situ radioimmunoassay as described by Helfman, et al. Proc. Nat'l Acad. Sci., (U.S.A.) 80: 31-35 (1983), as described by Enea et al, supra.

The bacteria were transferred onto 82 mM nitrocellulose filters (Millipore HATF Millipore, Bedford, Mass.). Replica filters were made and regrown on the tetracycline plates described above, at 37°C.

The bacterial colonies were lysed by placing the open petri dishes over 1 ml of chloroform for 15 minutes. The filters were then placed in individual petri dishes or pooled in trays containing 50 mm Tris-HCl (pH 7.5), 150 mM NaCl, 2 mM magnesium chloride, 0.1 mM PMSF (phenylmethylsulfonylfluoride, BRL) 3% BSA, 40 micrograms/ml lysosome, 1 microgram/ml, DNAase I and gently agitated at room temperature for 1 to 2 hours. The filters were rinsed in 50 mM Tris-HCl (pH 7.5), 150 mM NaCl for 1 to 2 hours and then incubated for 15 to 30 minutes in 50 mM Tris-HCl(pH 7.5), 150 mM NaCl, and 3% BSA. The filters were then incubated in a 50 ml volume with $50 \times 10^6$ cpm $[^{125}I]$-labelled monoclonal antibody 2A10 in 150 mM NaCl, 3% BSA with gentle rocking at room temperature overnight. The filters were washed extensively with 150 mM NaCl, 0.1% NP40 (Sigma), and 50 mM Tris-HCl (pH 7.5) air dried and mounted for autoradiography.

After screening approximately 10,000 colonies, one was found to react with the monoclonal antibody 2A10.

The clone was purified by streaking on LB plates (10% Bactotryptone, 50% yeast extract, 170 mM NaCl, 1.5% Bacto agar) containing 12.5 micrograms/ml of tetracycline.

A single colony was picked and tested by both the in situ radioimmunoassay procedure described above and the two-site radioimmunoassay (Ellis et al. Nature, Vol. 302: 536-538) (1983). In this procedure antibody 2A10 was adsorbed to the wells of a microtiter plate. Crude lysates of the bacterial clones to be tested were added to the wells and incubated for sufficient time to allow the immunoreactive protein present in the lysate to bind to the adsorbed monoclonal antibody. The wells were then washed to remove any contaminating proteins and radio-labelled monoclonal antibody 2A10 was added. The labelled antibody attached to the antigenic protein that is already bound to the surface of the microtiter well by the first monoclonal antibody. Extracts of LE 392 harboring the plasmid scored positive in this assay.

EXAMPLE VI

Nucleotide Sequencing of Clone p277-19

Plasmid DNA was prepared from LE392 (p277-19) using a modification of the method of Birnbaum et al. Nucleic Acid Research 7: 1515 -1523 (1979). Briefly, bacterial cells were grown in LB medium (containing 10g Bactotryptone, 5g Bacto yeast extract, 10g NaCl [adjusted to pH 7.5 with NaOH] per liter) either to saturation or to an optical density of OD-600 nm of approximately 0.4 in which case chloramphenicol was added to 0.17 mg/ml. The cultures were incubated by centrifugation and resuspended in approximately 20 volumes of 50mM glucose. 25mM Tris-HCl (pH 8), 10mM EDTA and 2 volumes of 0.2N NaOH and 1% SDS were added. After incubating the suspension on ice for 10 minutes, 1.5 volume of 5M potassium acetate (pH 4.8) was added. Following a 10 minute incubation on ice, the sample was centrifuged at 8,000 rpm for 60 minutes in a fixed angle Sorval rotor and the supernatant was collected and combined with 0.6 volumes of isopropanol. The precipitate was then resuspended in 10 mM Tris, 10 mM EDTA (pH 8.0) treated with RNase A (BRL; 20 micrograms/ml) and RNase T1 (BRL; 1 unit/ml) at 37°C for 45 minutes. Carbowax 8,000 (Dow Chemical Co., Midland, Mich.) and NaCl were added to 10% w/v and 0.4M respectively and the sample was incubated at 4°C overnight. The preparation was then centrifuged at 8,000 rpm for 10 minutes and the pellet resuspended in 10 mM Tris (pH 8), and 1 mM EDTA, extracted with phenol/chloroform (1:1 v/v) and precipitated with ethanol.

Physical mapping of p277-19 with restriction enzymes MspI, HinfI, ScaI, BglI, PstI, AluI and RsaI (from BRL and New England Biolabs) revealed that the plasmid had suffered a deletion from approximately nucleotide 3350 to nucleotide 3608 on the standard pBR322 map (Sutcliffe, J.G., Cold Spring Harbor Sympos. Quant. Biol., 43:77-90 (1979)). As a result of this deletion, the PstI site 3' to the insert was missing and the HinfI site at nucleotide 3362 was very close to the 3' end of the insert. The physical sequence map of the vector 5' to the insert was unaltered. These findings influenced the selection of the technique for sequencing the insert as described below.

Six micrograms of the plasmid DNA were digested for 2 hours at 37°C with 24 units of MspI (New England Biolabs, Beverly, Mass.) in a 35 microliter reaction volume containing 10 mM Tris-HCl (pH 7.5), 10 mM magnesium chloride and 1 mM DTT. The digested plasmid DNA was fractionated on a 1.2% low melting agarose (International Biotechnologies, Inc., New Haven, Conn.) gel. The largest fragment, approximately 700 base pairs in length, which was determined to contain DNA insert (via the physical mapping described above), gel by melting the agarose slice at 70°C, followed by three sequential phenol extractions, one chloroform extraction and 2 cycles of precipitation in ethanol containing 2M ammonium acetate. The DNA was resuspended in 10 microliters of water and stored at -20°C.

Approximately 1 microgram of the gel purified p277-19 DNA was digested in a 10 microliter reaction volume with six units of HinfI (BRL) at 37°C for one hour in Hin buffer (10 mM Tris-HCl, pH 7.5, 10 mM $MgCl_2$, 50 mM NaCl) and 1 mM DTT (dithiothreitol). The reaction was stopped by heating at 65°C for 10 minutes.

The HinfI-digested DNA was then end-labelled in a 20 microliter reaction volume by adding each of dGTP, dTTP, dCTP to 50 mM and 30 $\times 10^{-6}$ Ci alpha-$[^{32}P]$-dATP (3,000 Ci/millimole) in Hin buffer (described above) with one mM DTT and two units of the Klenow fragment of E. coli DNA Polymerase I (Boerhinger-Mannheim) at room temperature for 15 minutes. Two microliters of 0.5 mM dATP were added and the incubation continued at room temperature for 10 minutes. The reaction was stopped by heating at 65°C for 10 minutes.

The end-labelled DNA fragments were fractionated in a 2% low melting temperature agarose mini gel. The fragments were electroeluted from the gel by cutting out a small well in front of the leading edge of the two DNA bands, filling the wells with approximately 35 microliters running buffer(0.04M Tris-acetate, 0.002 M EDTA) and continuing electrophoresis with four 45-60 second pulses (60 volts). The buffer in the wells was collected and the wells were refilled between each pulse of current.

Six micrograms of salmon sperm DNA (Sigma) were added to the DNA fragments and the mixture was extracted once with phenol and chloroform (1:1 v/v) and once with chloroform, followed by precipitation with 2M ammonium acetate and ethanol.

The precipitated DNA was resuspended in 53 microliters of water and sequenced according to the method of Maxam and Gilbert, Methods in Enzymology, Vol. 65, 499-560 (1980). The details of this method are set forth in Table I, which is based on a table of Maniatis, et al., "Recombinant DNA: A Cloning Manual" Cold Spring Harbor (1980).

The p277-19 DNA fragment encoded a peptide which contained a series of tandem amino acid repeats. The repetitive unit of the peptide was four amino acids in length and consisted of proline, asparagine, alanine and asparagine repeated 23 times in tandem. The nucleotide sequence of the DNA fragment is illustrated in Fig. 1. The sequence is aligned as a matrix with the reading frame in register with that of the beta-lactamase. The sequence was derived according to the method of Maxam and Gilbert supra using the Hpa II site 5' to the PstI insert in pBR322 and a HinfI site 3' to the insert as labelling sites. Due to the 300 base pair deletion in the pBR322 on the 3' side of the insert, the Hinf I site has been brought to within 10 base pairs of the 3' end of the d(C)-tailed cDNA insert.

TABLE 1. SUMMARY OF BASE-SPECIFIC REACTIONS FOR SEQUENCING END-LABELLED DNA

| | G | G & A | T & C | C | A > C |
|---|---|---|---|---|---|
| Mix | 200 μl DMS buffer<br>10 μl [$^{32}$P]DNA | 10 μl H$_2$O<br>10 μl [$^{32}$P]DNA | 10 μl H$_2$O<br>10 μl [$^{32}$P]DNA | 15 μl 5 M NaCl<br>10 μl [$^{32}$P]DNA | 1 mg of salmon sperm DNA in each<br>100 μl $\begin{cases} 2\text{ N NaOH} \\ 1\text{ mM EDTA} \end{cases}$<br>1 μl [$^{32}$P]DNA |
| Chill to | 0°C | 0°C | 0°C | 0°C | Heat to 90°C 3-4 min. |
| Add | 1 μl DMS | 25 μl formic acid | 30 μl HZ | 40 μl HZ | 150 μl 1 N acetic acid<br>5 μl tRNA (1mg/ml)<br>750 μl 95% ethanol |
| Incubate | 20°C, 2-3 min. | 20°C, 5 min. | 20°C, 8 min. | 20°C, 12 min. | |
| Add | 50 μl HZ stop<br>750 μl ethanol | 200 μl HZ stop<br>750 μl ethanol | 200 μl HZ stop<br>750 μl ethanol | 200 μl HZ stop<br>750 μl ethanol | |
| Store | -70°C, 10-15 min. | -70°C, 10-15 min. | -70°C, 10-15 min. | -70°C, 10-15 min. | -70°C, 10 min. |
| Centrifuge | 10 min. | 10 min. | 10 min. | 10 min. | 10 min. |
| To pellet add | 250 μl 0.3 M NaAc<br>750 μl ethanol | 250 μl 0.3 M NaAc<br>750 μl ethanol | 250 μl 0.3 M NaAc<br>750 μl ethanol | 250 μl 0.3 M NaAc<br>750 μl ethanol | 250 μl 0.3 M NaAc<br>750 μl ethanol |
| Store | -70°C, 10-15 min. | -70°C, 10-15 min. | -70°C, 10-15 min. | -70°C, 10-15 min. | -70°C, 10-15 min. |

TABLE 1. CONTINUED

|  | G | G + A | T + C | C | A + C |
|---|---|---|---|---|---|
| Centrifuge | 10 min. | 10 min. | 10 min. | 10 min. | 10 min. |
| Rinse pellet with 70% ethanol | 70% ethanol | 70% ethanol | 70% ethanol | 70% ethanol | 70% ethanol |
| Vacuum dry |  |  |  |  |  |
| To pellet add | 100 μl 1.0 M piperidine | 100 μl 1.0 M piperidine | 100 μl 1.0 M piperidine | 100 μl 1.0 M piperidine | 100 μl 1.0 M piperidine |
| Heat to | 90°C, 30 min. | 90°C, 30 min. | 90°C, 30 min. | 90°C, 30 min. | 90°C, 30 min. |
| Lyophilize |  |  |  |  |  |
| Add | 20 μl H₂O | 20 μl H₂O | 20 μl H₂O | 20 μl H₂O | 20 μl H₂O |
| Lyophilize |  |  |  |  |  |
| Add | 10 μl H₂O | 10 μl H₂O | 10 μl H₂O | 10 μl H₂O | 10 μl H₂O |
| Lyophilize |  |  |  |  |  |
| Add | 10 μl loading buffer | 10 μl loading buffer | 10 μl loading buffer | 10 μl loading buffer | 10 μl loading buffer |
| Vortex |  |  |  |  |  |
| Heat to |  |  |  |  |  |
| Chill in ice | 90°C, 1 min | 90°C, 1 min | 90°C, 1 min | 90°C, 1 min | 90°C, 1 min |
| Load onto Gel |  |  |  |  |  |

Reactions should be carried out in siliconized Eppendorf tubes.

EXAMPLE VII

Presence of Repetitive Epitopes in the Immunodominant Region of CS Proteins of P. falciparum.

The presence of repetitive epitopes in P. falciparum CS proteins was confirmed by performing a two-site immunoradiometric assay with a single monoclonal antibody. This is illustrated in Figure 2A and 2B.

In this assay wells of flexible microtiter plates (Dynatech Inc.) were coated with 20 micrograms/ml anti-Plasmodium falciparum monoclonal antibody (2A10). After repeated washes with phosphate buffered saline containing 1% bovine serum albumin, the wells were incubated with two fold serial dilutions of lysates of E. coli LE 392, containing plasmid p277-19 or E. coli LE 392 containing the pBR322 vector. Following a two hour incubation at room temperature, the wells were washed and 30 microliters of [$^{125}$I]-labeled monoclonal antibody 2A10 (1 X $10^5$ cpm; specific activity 2 x $10^7$ cpm/microgram) were added. After an incubation for one hour at room temperature, the wells were washed with PBS-Tween 20-BSA, dried and counted in a gamma counter. Lysates of E. coli LE 392 containing plasmid p277-19 were also tested using monoclonal antibody 2A10 coated plates and an unrelated [$^{125}$I]-labeled monoclonal antibody (X-X). As illustrated in Fig. 2A, the recombinant protein expressed by clone p277-19 simultaneously binds both the immobilized and the radiolabeled antibody. This indicates that the recombinant protein, like the authentic CS protein, contains at least two epitopes which are recognized by the anti-CS monoclonal antibody 2A10.

EXAMPLE VIII

Inhibitory Effect of Bacterial Extracts Made from LE 392 (p277-19) of the Binding of Labeled Monoclonal Antibody to the Epitopes of Authentic P. falciparum CS Proteins

The following inhibition assay was performed. 10 microliters (5 X $10^4$ cpm) of [$^{125}$I]-labeled monoclonal antibody 2A10 were incubated with 30 microliters of two fold serial dilutions of lysates of E. coli LE 392 containing plasmid p277-19 (O-O) or *E. coli* LE 392
containing the pBR322 vector (X-X). Following a thirty-
minute incubation at room temperature, 30 microliters
of these mixtures were transfered into microtiter plates
previously coated with an extract of *P. falciparum*
sporozoites (Zavala et al., J. Exp. Med. 157:1947 (1983)).
After a one hour incubation period the wells were washed,
dried and counted in a gamma counter. The results of
this inhibitory assay are illustrated in Fig 2B. The
results show that bacterial extracts made from LE 392
containing the plasmid p277-19 inhibit the binding
of labeled monoclonal antibody to the epitopes of native
*P. falciparum* CS proteins. The specificity of this
reaction was confirmed by a further experiment in which
it was shown that cell extracts of p277-19 did not
inhibit the binding of an anti-*Plasmodium berghei* mono-
clonal antibody to the corresponding CS protein. These
data show that the recombinant protein encoded by
p277-19 exhibits the antigenic feature of the *P. falciparum*
CS protein.

EXAMPLE IX

Amino Acid Sequence of the 4-Amino Acid Repeat

The nucleotide sequence of the p277 19 insert
was derived according to the method of Maxam and Gilbert,
Proc. Nat'l. Acad.(USA) 74:560 (1977) using the Hpa II
site 5' to the PstI site insert in pBR322 and a HinfI
site 3' to the insert as labelling sites. The nucleotide
sequence of the p277-19 insert is illustrated in Fig.
1. The method followed is described in detail in Table I.

The deduced amino acid sequence of the four
amino acid repeat set forth below is based upon translation
of the nucleotide sequence in the correct reading frame:
Pro-Asn-Ala-Asn. (All sequences are expressed from the
end nearest the $NH_2$ terminus on the left to the end
nearest the -COOH terminus on the right.)

The four amino acid sequence is repeated twenty-
three times in tandem. However, at the nucleotide level,
the repeats in p277-19 consist of eight variants. Both of the asparagine codons, three of the four proline codons, and two of the four alanine codons are used (Fig. 1). This repetitive pattern of four amino acids is shorter than any of the three known CS protein repeats. The repeats of P. knowlesi and P. cynomolgi (Gombak strain), two simian malaria parasites, are twelve and eleven amino acids long, respectively (Godson, et al. Nature 305:29 (1983); V. Enea et al. PNAS submitted (1984).

Although neither the DNA nor the protein sequences of these three sets of repeats exhibit extensive homology, they have similarities in their amino acid composition. Alanine and asparagine are present in the repeats of all three CS proteins; proline is present in P. knowlesi and P. falciparum; and glutamic acid and glycine are present in P. knowlesi and P. cynomolgi (Gombak).

The CS protein of P. falciparum appears to be encoded by a single copy gene based on the results of genomic DNA mapping experiments. In outline, the genomic clone was mapped as follows:

P. falciparum DNA obtained from blot stages was digested with restriction enzymes (including EcorI, BamhI, HindIII, BglII, SalI, XhoI) fractionated on agarose gel, transferred to a nitrocellulose filter, hybridized with $[^{32}P]$-labeled p277-19 and autoradiographed. This procedure permits the determination of the sizes of the P. falciparum DNA (generated by all the above restriction fragments) that bears homology to the radioactive probe. Specifically, the SalI digest generated a fragment of approximately 7,000 nucleotides that hybridized with the probe. Since a fragment of this size was significantly smaller than the bulk of the fragments generated by SalI, a size-fractionation of SalI-digested DNA was undertaken to obtain the 7,000 nucleotide fragment generated by SalI which was expected to constitute a significant enrichment for the CS-gene.

SalI-digested DNA was fractionated on a sucrose gradient (10-40% w/v in 1M NaCl, 2mM Tris-HCl (pH 8) and 5mM EDTA; SW-41) at 38,000 rpm at 20°C for 16.5 hours. The fractions were collected and aliquots were hybridized to [$^{32}$P]-labelled p277-19.

The fraction that contained the CS sequence was ligated to SalI-digested EMBL4-DNA. (EMBL4 is a derivative of phage lambda; other SalI-digested phage lambda DNA vectors could have been employed, such as Charon 28 obtainable from BRL.)

The ligate was packaged _in vitro_ (packaging extracts and protocols are commercially available from BRL and other sources) and plated on LE 392. The resulting plaques were screened with [$^{32}$P]-labelled p277-19. Two independent positive plaques were thus identified.

Characterization of the isolates is conducted by well-known techniques and includes physical mapping of the phages, subcloning of specific DNA fragments into plasmid vectors, determination of the DNA sequence of these fragments and, if necessary, mapping experiments with the messenger RNA of the _P. falciparum_ CS protein. Using this procedure, the gene coding for the entire CS-protein of _P. falciparum_ is isolated and sequenced.

EXAMPLE X
Synthesis of Peptides Having the Repeating Amino Acid Sequence

To confirm that the preceding amino acid sequence contains the immunoreactive site, a corresponding synthetic peptide has been synthesized using solid phase resin synthesis (Marglin, B. and Merrifield, R. B., Ann. Rev. Bio. Chem. 39:841-866 (1970). The general steps of the peptide synthesis techniques used herein are well known. The synthesis was carried out using a benzhydrylamine (BHA) resin on an automated synthesizer controlled by a computer using a program based on that of Merrifield, R. B., Fed. Proc. 21:412 (1962); J. Chem. Soc. 85:2149, (1963). The four amino acid repeat was assembled on the benzhydrylamine resin. The tandem repeat was assembled by the sequential addition of protected amino acids in the same order as the four amino acid repeat, using the method described above. Amino acid composition and sequence analysis performed by automated Edman degradation confirm that the peptide had been correctly synthesized. A 12-MER peptide was thus synthesized which consisted of three sequential repeats of the minimum repeating unit (Pro-Asn-Ala-Asn).

To confirm that the correct epitope has been obtained, rabbits are immunized with a peptide consisting of three and six tandem repeats of the four amino acids coupled to a carrier (bovine gamma globulin in complete Freund's adjuvant). Four weeks after the injection, the rabbits are bled and their serum assayed for the presence of antibodies against the tandemly repeated peptides and against extracts of P. falciparum sporozoites. The results show that the animals produce high titers (greater than 1:1000) of antibodies to the native CS protein present in the parasite extracts.

EXAMPLE XI
Inhibition of the Binding of Monoclonal Antibody
To Authentic P. falciparum Antigen by the
Synthetic Peptide The antigenicity of a synthetic 12-amino acid peptide consisting of a 3X tandem repeat of the minimum repeating unit (Pro-Asn-Ala-Asn) of the P. falciparum CS protein was confirmed by a direct radioimmunoassay, as follows:

P. falciparum sporozoite extract was used to coat the bottom of microtiter well plates (as previously described). Unbound native antigen was removed by washing and the wells were filled with serial dilutions of PBS-BSA containing serial dilutions of the synthetic 12-amino acid peptide having the sequence (Pro-Asn-Ala-Asn-Pro-Asn-Ala-Asn-Pro-Asn-Ala-Asn.) Control wells were filled with serial dilutions of PBS-BSA containing the synthetic 12-amino acid peptide representing the epitope of P.

knowlesi, i.e. (Gln-Ala-Gln-Gly-Asp-Gly-Ala-Asn-Ala-Gly-Gln-Pro). Saturation amounts of [$^{125}$I]-labelled monoclonal antibody 2A10 were then added to the wells (8 x $10^4$ cpm) and allowed to bind. After removal of the supernatant residual radioactivity was measured with a gamma counter. The results are shown in Table II.

TABLE II

| Well No. | 1 | 2 | 3 | 4 | 5 | 6 |
|---|---|---|---|---|---|---|
| (1) P. falciparum 12-peptide (micrograms/ml) | 500 | 50 | 5 | 0.5 | 0.05 | 0.005 |
| (2) Residual Radioactivity of (1) (cpm) | 194 | 297 | 1590 | 4990 | 6092 | 6271 |
| (3) Non-Specific Antigen (P. knowlesi 12-peptide) (micrograms/ml) | 500 | 50 | 5 | 0.5 | 0.05 | 0.005 |
| (4) Residual Radioactivity of (3) (cpm) | 5179 | 5838 | 6170 | 6409 | 6174 | 6181 |

Control on wells coated with BSA alone without sporozoite extract showed a residual radioactivity of 27-58 cpm.

The above results show that the monoclonal antibody recognizes and quantitatively binds to the synthetic 12-amino acid peptide.

EXAMPLE XII

Recognition of the Synthetic Peptide By Monoclonal Antibodies to P. falciparum CS-Protein Another immunoradiometric assay was used to show that the synthetic 12-amino acid peptide is recognized by several antibodies to P. falciparum CS protein. The antibodies used are designated 2A10, 1E9, 3D6, and 2C11.

A synthetic 12-MER peptide (three repeats of the pro-asn-ala-asn peptide) (20 micrograms/ml) was bound to the bottom of microtiter wells as previously described. The wells were saturated with BSA.

Serial dilutions of each type of unlabelled monoclonal antibody preparation (10 micrograms/ml) in serial dilution were introduced into separate 12-MER coated wells, and sufficient time was allowed for the antibody to bind to the coat.

Finally, after washing the wells, saturation amounts of affinity-purified, radiolabeled goat anti-mouse IgG were also introduced into the wells and allowed to bind to the monoclonal antibodies bound to the peptide coat. The wells were then washed and residual radioactivity was measured in a gamma counter. The results are summarized in Table III below.

Unlabelled monoclonal antibodies to P. knowlesi, BSA coated wells (in the absence of anti-P. falciparum monoclonal antibody) and 12-amino acid peptide coated wells (in the absence of anti-P. falciparum monoclonal antibody) were used as controls. Controls showed 40-100 cpm.

TABLE III

| Well No. | 1 | 2 | 3 | 4 | 5 |
|---|---|---|---|---|---|
| Unlabelled Antibody (micrograms/ml) | 10 | 0.1 | 0.01 | 0.001 | $1 \times 10^{-4}$ |

Residual Radioactivity (cpm)

| | | | | | |
|---|---|---|---|---|---|
| 2A10 | 1844 | 775 | 96 | 90 | 71 |
| 1E9 | 3787 | 2475 | 888 | 176 | 86 |
| 3D6 | 457 | 119 | 121 | 83 | 78 |
| 2C11 | 2874 | 1761 | 863 | 296 | 107 |

The controls in which the wells were incubated using dilutions of three other non-specific monoclonal antibodies of the same isotype resulted in residual radioactivity ranging between 44 and 100.

The above results show that several monoclonal anti-P. falciparum antibodies recognize and bind quantitatively to the synthetic 12-amino acid peptide.

EXAMPLE VIII

Immunization with the Synthetic Repeated Epitope of P. falciparum (12 MER and 24 MER)

A tandemly repeated peptide (3X and 6X) is synthesized as described above, except a cysteine residue is added at the N-terminus. To determine whether the synthesis had been performed correctly, an aliquot is subjected to acid hydrolysis at reduced pressure (5.6M HCl 110°C, 72 hours) and its amino acid composition is determined. The peptide is coupled to a carrier protein (e.g. keyhole limpet hemocyanin, or tetanus toxoid, through its N terminal cysteine residue, using a m-malemidolbenzoyl-N-hydroxysuccinimide ester (MBS) as the coupling reagent (Ling et al, Biochemistry 18, 690 (1979)).

This is a bifunctional reagent which under appropriate conditions reacts with the amino group of the carrier and with the third group of the peptides. 4 mg of the carrier protein in 0.25 ml of 0.05 $PO_4$ buffer, pH 7.2, is reacted dropwise with 0.7 mg MBS dissolved in dimethyl formamide and stirred for 30 minutes at room temperature. The product MB carrier is separated from the unreacted chemicals by passage in a Sephadex C-25 column equilibrated in 0.05 M $PO_4$ buffer, pH 6.0. The MB carrier is then reacted with 5 mg of the 12- or 24-MER containing compound, dissolved in PBS (pH 7.4.) The mixture is stirred for 3 hours at room temperature and coupling is monitored with radioactive peptide. The conjugate is dialyzed and used as a vaccine for administration to non-human primates in a physiologically acceptable medium.

Alternatively, the tandemly repeated peptide (3X) can be further polymerized with glutaraldehyde as follows: Dissolve 20 mg of peptide in 10 ml of phosphate buffered saline (PBS). Make fresh glutaraldehyde from a stock with 13 milliliters of PBS. Stir the peptide and glutaraldehyde overnight at room temperature. Neutralize the excess glutaraldehyde with 1M ethanolamine. Separate the polymerized peptide by high performance liquid chromatography (HPLC) using sizing columns, and dialyze repeatedly against water. This is then used in a vaccine preparation.

Five chimpanzees are immunized with 200 micrograms of the conjugated protein or the polymerized product absorbed to aluminum hydroxide gel. Their serum is monitored for the presence of antibodies to CS proteins of P. falciparum using an immunoradiometric assay. Serum dilutions are incubated in antigen-coated wells of microtiter plates. The presence of chimpanzee antibody bound to the solid-phase antigen is monitored by incubation with [$^{125}$I]-labeled affinity-purified rabbit-anti-human IgG (which strongly cross-reacts with chimpanzee IgG).

After 30 days, the serum titer of the chimpanzees rises to titers of greater than 1/1000. At this time, these chimpanzees (as well as five other control chimpanzees injected with non-conjugated carrier protein adsorbed to aluminum hydroxide) are challenged with 2,000 viable P. falciparum sporozoites. The infection is monitored daily for a total of 30 days by microscopic examination of blood smears, starting one week after the inoculation of the parasites. The results show that the five chimpanzees immunized with the vaccine (conjugated protein) are totally protected, that is, no parasites are found in their blood. In contrast, the control chimpanzees have trophozoites of P. falciparum in their circulation 10-12 days after challenge. Based on the close similarities of human and chimpanzee immune responses and on the fact that protection immunity has been obtained in humans by injection of inactivated sporozoites of P. falciparum, the results obtained upon immunization of chimpanzees with the described synthetic peptide will also be obtained following similar treatment of human patients.

A peptide comprising an epitope of a sporozoite CS protein of a member of the species Plasmodium falciparum and having a tandemly repeating sequence of four amino acids, said tandem repeat having a combined molecular weight of less than 3,000.

```
              Pro   Asn   Ala   Asn
       15
      G     CCA   AAT   GCA   AAC
             C     T     A     C
             A     C     A     C
             C     T     A     T
             T     T     A     C
             C     T     A     T
             T     T     A     T
             T     T     C     T
             A     T     A     T
             T     T     A     C
             C     T     A     T
             T     T     A     T
             T     T     C     T
             A     T     A     T
             A     T     A     C
             A     C     A     C
             C     T     A     T
             T     T     C     T
             A     T     A     T
             A     T     A     C
             A     T     A     C
             A     T     A     C
             C     T     A     T
            CCT   AAT   AAA   AAC      18
            AAT   CAA   GCC   CCC    C
```

FIG 1

A peptide comprising an epitope of a sporozoite CS protein of a member of the species *Plasmodium falciparum* and having a tandemly repeating sequence of four amino acids, said tandem repeat having a combined molecular weight of less than 3,000. --

What is claimed is:

1. A peptide antigen comprising an amino acid sequence consisting essentially of a non-repetitive epitope of the circumsporozoite protein of a parasite of the genus plasmodium, said peptide having the property of eliciting formation of antibodies that bind to said non-repetitive epitope on the parasite surface, said peptide being synthetic, essentially purified, and substantially shorter in length than said protein.

2. The peptide of claim 1, where said sequence consists essentially of the sequence of a segment of the amino acid sequence of said circumsporozoite protein said segment lying within a charged domain of said protein and lying outside of, but proximately to, an immunodominant epitope repeat region of said protein.

3. The peptide of claim 2, wherein said charged domain is proximal to the N-terminal of said protein in relation to said immunodominant epitope.

4. The peptide of claim 2, wherein said charged domain is proximal to the C-terminal of said protein in relation to said immunodominant epitope.

5. The peptide of claim 3, wherein said protein is *P. knowlesi* circumsporozoite protein.

6. The peptide of claim 4, where said protein is *P. knowlesi* circumsporozoite protein.

7. The peptide of claim 3, wherein said protein is *P. falciparum* circumsporozoite protein.

8. The peptide of claim 4, wherein said protein is *P. falciparum* circumsporozoite protein.

9. The peptide of claim 5, wherein said epitope consists essentially of the amino acid sequence from N to C terminal:

Pro-Lys-Lys-Pro-Asn-Glu-Asn-Lys-Leu-Lys-Gln-Pro-Asn-Glu.

10. The peptide of claim 6, said epitope consisting essentially of the amino acid sequence from N to C terminal:

(Arg-Arg-Lys-Ala-His-Ala-Gly-Asn-Lys-Lys-Ala-Glu-Asp-Leu-Thr-Met-Asp-Asp-Leu-Gln).

11. The peptide of claim 7, said epitope consisting essentially of the amino acid sequence from N to C terminal:

Arg-Lys-Pro-Lys-His-Lys-Lys-Leu-Lys-Gln-Pro-Gly-Asp.

12. The peptide of claim 8, said epitope consisting essentially of the amino acid sequence from N to C terminal:

Lys-Pro-Gly-Ser-Ala-Asn-Lys-Pro-Lys-Asp-Glu-Leu-Ile-Tyr-Glu-Asn-Asp-Ile-Glu.

13. A vaccine against malaria comprising a peptide said peptide comprising an amino acid sequence consisting essentially of a non-repetitive epitope of the circumsporozoite protein of a member of the genus plasmodium, said peptide having the property of eliciting formation of antibodies that bind to the parasite surface and that neutralize the circumsporozoite protein, said peptide being substantially shorter in length than said protein, essentially purified, and covalently linked to a carrier in a pharmaceutically acceptable medium.

14. The vaccine of claim 13 said epitope lying within a charged domain of said protein and outside of but proximately to the immunodominant epitope region of said protein and proximally to the N-terminal of said protein in relation to said immunodiminant epitope.

15. The vaccine of claim 13 said epitope lying within a charged domain of said protein and outside of but proximately to the immunodominant epitope region of said protein and proximal to the C-terminal of said protein in relation to said immunodominant epitope.

16. The vaccine of claim 14 wherein said epitope consists essentially of a sequence selected from the group consisting of Pro-Lys-Lys-Pro-Asn-Glu-Asn-Lys-Leu-Lys-Gln-Pro-Asn-Glu and (Arg-Lys-Pro-Lys-His-Lys-Lys-Leu-Lys-Gln-Pro-Gly-Asp.

17. The vaccine of claim 15 wherein said epitope consists essentially of a sequence selected from the group consisting of Arg-Arg-Lys-Ala-His-Ala-Gly-Asn-Lys-Lys-Ala-Glu-Asp-Leu-Thr-Met-Asp-Asp-Leu-Gln and Lys-Pro-Gly-Ser-Ala-Asn-Lys-Pro-Lys-Asp-Glu-Leu-Ile-Tyr-Glu-Asn-Asp-Ile-Glu.

18. A method of raising antibodies to a circumsporozoite protein of a member of the genus plasmodium, said method comprising administering to a host an antibody-eliciting-effective amount of the peptide of claim 1.

19. A method of raising antibodies to a circumsporozoite protein of a member of the genus plasmodium, said method comprising administering to a host an antibody-eliciting-effective amount of the peptide of claim 5.

20. A method of raising antibodies to a circumsporozoite protein of a member of the genus plasmodium, said method comprising administering to a host an antibody-eliciting-effective amount of the peptide of claim 6.

21. A method of raising antibodies to a circumsporozoite protein of a member of the genus plasmodium, said method comprising administering to a host an antibody-eliciting-effective amount of the peptide of claim 7.

22. A method of raising antibodies to a circumsporozoite protein of a member of the genus plasmodium, said method comprising administering to a host an antibody-eliciting-effective amount of the peptide of claim 8.

23. A peptide according to claim 1, said peptide being capable of eliciting formation of antibodies recognizing said protein as well as circumsporozoite proteins from other members of the genus plasmodium.

24. The peptide of claim 1, wherein said synthetic peptide is synthesized chemically.

* * * * *